(12) United States Patent
Rinehart et al.

(10) Patent No.: US 7,115,743 B2
(45) Date of Patent: Oct. 3, 2006

(54) METABOLITES OF ECTEINASCIDIN 743

(75) Inventors: Kenneth L. Rinehart, Urbana, IL (US); Jose J. Morales, Urbana, IL (US); Joel Reid, Rochester, MN (US); Isabel Reymundo, Madrid (ES); Pablo Floriano, Madrid (ES); Lola Garcia Gravalos, Madrid (ES)

(73) Assignee: Pharma Mar, S.A., Madrid ( * ) Notice: Subject to any disclaimer, the term of this patent is extended or adjusted under 35 U.S.C. 154(b) by 0 days.

(21) Appl. No.: 11/009,237

(22) Filed: Dec. 10, 2004

(65) Prior Publication Data

US 2005/0261326 A1 Nov. 24, 2005

Related U.S. Application Data

(63) Continuation of application No. 09/971,852, filed on Oct. 3, 2001, now Pat. No. 6,867,334, which is a continuation of application No. 09/309,947, filed on May 11, 1999, now Pat. No. 6,316,214.

(60) Provisional application No. 60/085,024, filed on May 11, 1998.

(51) Int. Cl.
*C07D 221/18* (2006.01)
(52) U.S. Cl. ...................................... 546/38
(58) Field of Classification Search ................ 546/38
See application file for complete search history.

(56) References Cited

U.S. PATENT DOCUMENTS

| | | | |
|---|---|---|---|
| 4,273,773 A | 6/1981 | Demerson et al. | |
| 5,089,273 A | 2/1992 | Rinehart et al. | |
| 5,149,804 A | 9/1992 | Rinehart et al. | |
| 5,256,663 A | 10/1993 | Rinehart et al. | |
| 5,459,141 A | 10/1995 | Vertesy et al. | |
| 5,478,932 A | 12/1995 | Rinehart et al. | |
| 5,484,717 A | 1/1996 | Zaccardi | |
| 5,654,426 A | 8/1997 | Rinehart et al. | |
| 5,721,362 A | 2/1998 | Corey et al. | |
| 5,985,876 A | 11/1999 | Rinehart et al. | |
| 6,124,292 A | 9/2000 | Corey | |
| 6,316,214 B1 * | 11/2001 | Rinehart et al. | 435/25 |
| 6,348,467 B1 | 2/2002 | Corey | |
| 6,686,470 B1 | 2/2004 | Danishefsky et al. | |
| 6,867,334 B1 * | 3/2005 | Rinehart et al. | 568/584 |
| 2003/0216397 A1 | 11/2003 | Flores et al. | |
| 2004/0002602 A1 | 1/2004 | Francesch et al. | |
| 2004/0019056 A1 | 1/2004 | Manzanares et al. | |

FOREIGN PATENT DOCUMENTS

| | | |
|---|---|---|
| EP | 0 309 477 B1 | 11/1991 |
| JP | 59-225189 | 12/1984 |
| JP | 60-84288 | 5/1985 |
| WO | WO 87/07610 | 12/1987 |
| WO | WO 92/09607 | 6/1992 |
| WO | WO 98/12198 | 3/1998 |
| WO | WO 98/46080 | 10/1998 |
| WO | WO 99/58125 | 11/1999 |

(Continued)

OTHER PUBLICATIONS

Sparidans R. et al. Search for Metabolites of Ecteinascidin 743. Anti-Cancer Drugs 12(8)653-666, 2001.*
Arai, T. et al., "The Structure of a Novel Antitumor Antibiotic, Saframycin A", *Experientia*, vol. 36, pp. 1025-1027 (1980).

(Continued)

*Primary Examiner*—Ralph Gitomer
(74) *Attorney, Agent, or Firm*—Fish & Richardson P.C.

(57) ABSTRACT

The purification and structure elucidation of several products of the metabolism of Et 743 by human cytochrome CYP3A4 have been accomplished. These compounds are abbreviated herein as "ETM" followed by a numeric value which represents the approximate molecular weight. Three compounds have been identified to date, namely ETM 305, ETM 775 and ETM 204. The structures of these ecteinascidin metabolites are as follows:

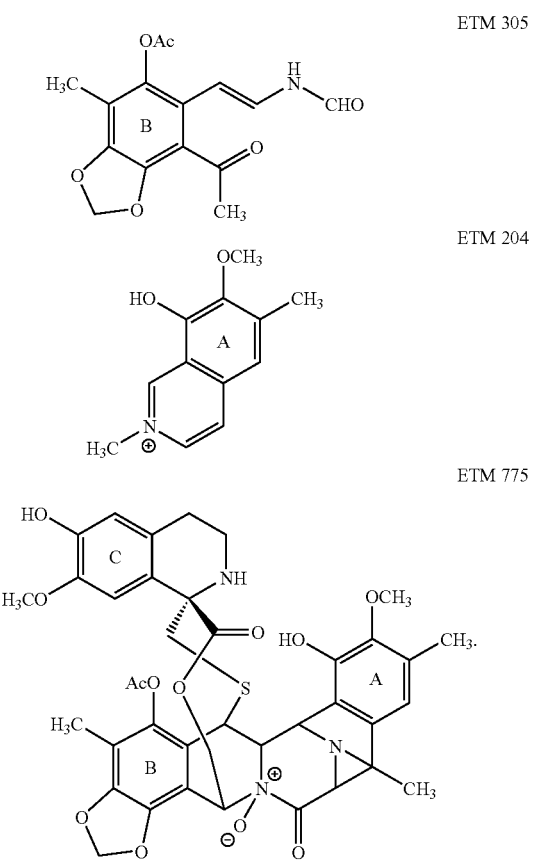

2 Claims, 25 Drawing Sheets

FOREIGN PATENT DOCUMENTS

| WO | WO 00/18233 | 4/2000 |
|---|---|---|
| WO | WO 00/69862 | 11/2000 |
| WO | WO 01/77115 | 10/2001 |
| WO | WO 01/87894 | 11/2001 |
| WO | WO 01/87895 | 11/2001 |

OTHER PUBLICATIONS

Arai, Tadashi et al., "Directed Biosynthesis of New Saframycin Derivatives with Resting Cells of Streptomyces lavendulae", *Antimicrobial Agents and Chemotherapy*, vol. 28, No. 1, pp. 5-11 (1985).

Arai, Tadashi et al., "Increased Production of Saframycin A and Isolation of Saframycin S", *The Journal of Antibiotics*, vol. XXXIII, NO. 9, pp. 951-960 (1980).

Arai, Tadashi et al., "Increased Production of Saframycin A and Isolation of Saframycin S", *The Journal of Antibiotics*, vol. XXXIII, No. 9, pp. 951-960 (1980).

Arai, Tadashi er al., "Isoquinolineinones from Actinomycetes and Sponges", *The Alkaloids Chemistry and Pharmacology*, vol. XXI, pp. 56-100 (1983).

Arai, Tadashi et al., "New Antibiotics, Safraycins A, B, C, D and E", *The Journal of Antibiotics*, vol. XXX, No. 11, pp. 1015-1018 (1977).

Asaoka, Takemitsu et al., "A New Saframycin, Saframycin R", *The Journal of Antibiotics* vol. XXXV, No. 12, pp. 1708-1710 (1982).

Barton, Derek H.R. et al, "Synthesis and Properties of a Series of Sterically Hindered Guanidine Bases[1]", *Journal of the Chemical Society Perkin Transactions I*, No. 9, pp. 2085-2090 (1982).

Brown, J.M., "NCI's Anticancer Drug Screening Program May Not Be Selecting for Clinically Active Compounds," Oncol. Res. 9(5):213-215 (1997).

Cable, Karl M. et al., "The Biosynthesis of Tuberin from Tyrosine and Glycine; Observations on the Stereochemistry Associated with the Conversion of Glycine through Methylenetetrahydrofolate into Methenyltetrahydrofolate", *Journal of the Chemical Society Perkins Transactions I*, No. 7, pp. 1593-1598 (1987).

Cooper, Raymond et al., "Structure of the Quinone Antibiotic EM5519 and the Behavior of Quinones in Fast Atom Bombardment Mass Spectrometry", *The Journal of Antibiotics*, vol. XXXVIII, No. 1, pp. 24-30 (1985).

Corey, E.J. et al., "Enantioselective Total Synthesis of Ecteinascidin 743", *Journal of the American Chemical Society*, vol. 118, No. 38, pp. 9202-9203 (1996).

Cuevas, Carmen et al., "Synthesis of Ecteinascidin ET-743 and Phthalascidin Pt-650 from Cyanosafracin B", *Organic Letters*, vol. 2, No. 16, pp. 2545-2548 (2000).

Draetta, G. and Pagano, M., "Annual Reports in Medicinal Chemistry, vol. 31," Academic Press, San Diego, pp. 241-246 (1996).

Eckhardt, S.G. et al., "Activity of ecteinascidin, a novel marine cytotoxic, against primary human tumor colony-forming units", *Proceedings of the American Association for Cancer Research*, vol. 37, #2791, pp. 409 (1996).

Faircloth, G. et al., "Ecteinascidin-743 (ET743): in vitro (IVT) and in vivo (INV) Results in Tumor Models", *The European Journal of Cancer*, vol. 32A, Supp. 1, #24 O, pp. S5 (1996).

Flam, Faye, "Chemical Prospectors Scour the Seas for Promising Drugs", *Science*, vol. 266, pp. 1324-1325 (1994).

Frincke, James M. et al., "Antimicrobial Metabolites of the Sponge Reniera sp.", *Journal of the American Chemical Society*, vol. 104, pp. 265-269 (1982).

Fukuyama, Tohru et al., "Total Synthesis of (±)-Saframycin A", *Journal of American Chemical Society*, vol. 112, pp. 3712-3713 (1990).

Fukuyama, Tohru et al., "Stereocontrolled Total Synthesis of (±)-Saframycin B", *Journal of American Chemical Society*, vol. 104, pp. 4957-4958 (1982).

Garcia-Rocha, M. et al., "Characterisation of antimitotic products from marine organisms that disorganize the mirotubule network: ecteinascidin 743, isohomohalichondrin-B and LL-15", *British Journal of Cancer*, vol. 73, pp. 875-883 (1996).

Goldwasser, F, et al. "Characterization of ecteinascidin 743-induced DNA damages in cells", *Proceedings of the American Association for Cancer Research*, vol. 39, #4066, pp. 598 (1998).

Guan, Yue et al., "Molecular and Crystal Structures of Ecteinascidins: Potent Antitumor Compounds from the Caribbean Tunicate Ecteinascidia Turbinata", *Journal of Biomolecular Structure & Dynamics*, vol. 10, No. 5, pp. 793-818 (1993).

Gulavita, Nanda K., et al., "Antimicrobial Constituents of a Sponge-Nudibranch Pair from Sri Lanka", *Bioactive Compounds from Marine Organisms*, Oxford & IBH Publishing Co. Pvt. Ltd., pp. 229-233 (1991).

He, Hai-yin et al., "Renieramycins E and F from the Sponge Reniera sp.: Reassignment of the Stereochemistry of the Renieramycins", *The Journal of Organic Chemistry*, vol. 54, No. 24, pp. 5822-5824 (1989).

Hendriks, H.R. et al., "High antitumor activity of ET743 in human tumor xenograft models", *Proceedings of the American Association for Cancer Research*, vol. 37, #2653, pp. 389 (1996).

Ikeda, Yoshifumi et al., "Safracins, New Antitumor Antibiotics I. Producing Organism, Fermentation and Isolation", *The Journal of Antibiotics*, vol. XXXVI, No. 10, pp. 1279-1283 (1983).

Ikeda, Yoshifumi et al., "Safracins, New Antitumor Antibiotics I. Producing Organism, Fermentation and Isolation", *The Journal of Antibiotics*, vol. XXXVI, No. 10, pp. 1284-1289 (1983).

Koenig, Karl E., "The Applicability of Asymmetric Homogeneous Catalytic Hodrogenation", *Asymmetric Synthesis*, Ed. Morrison, Academic Press, Inc., Orlando, FL, vol. 5, pp. 71 (1985).

Kofron, William G. et al., "A Convenient Method for Estimation of Alkyllithium Concentrations", *The Journal of Organic Chemistry*, vol. 41, No. 10, pp. 1879-1880 (1976).

Kubo, Akinori et al., "Structure of Saframycin D, A New Dimeric Isoquinolinequinone Antibiotic", *Chem. Pharm. Bull.*, vol. 35, No. 1, pp. 440-442 (1987).

Kuffel, M.J. et al., "Cytochrome P450 catalyzed metabolism of Ecteinascidin 743 by rat and human liver microsomes", *Proceedings of the American Association for Cancer Research*, vol. 38, #4003, pp. 596 (1997).

Ito, Yoichiro, "High-Speed Countercurrent Chromatography", *Critical Reviews in Analytical Chemistry*, vol. 17, No. 1, pp. 65-143 (1986).

Lichter, W. et al., "Biological Activities Exerted by Extracts of Ecteinascidia Turbinata", *Food and Drugs from the Sea Proceedings*, pp. 117-127 (1972).

Lown, J. William et al., "Structure and Confirmation of Saframycin R Determined by High Field $^1$H and $^{13}$C NMR and its Interactions with DNA in Soloution", *The Journal of Antibiotics*, vol. XXXVI, No. 9, pp. 1184-1194 (1983).

Lown, J. William et al., "Molecular Mechanisms of Binding and Single-Strand Scission of Deoxyribonucleic Acid by the Antitumor Antibiotics Saframycins A and C", *Biochemistry*, vol. 21, No. 3, pp. 419-428 (1982).

Martinez, Eduardo J. et al., "Phthalascidin, a synthetic antitumor agent with potency and mode of action comparable to ecteinascidin 743", *Chemistry*, vol. 96, pp. 3496-3501 (1999).

Mikami, Yuzuru et al., "Structural Studies on Minor Components of Saframycin Group Antibiotics Saframycins F, G and H", *The Journal of Antibiotics*, vol. XLI, No. 6, pp. 734-740 (1988).

Mirsalis, J.C. et al., "Toxicity of Ecteinascidin 743 in female Fischer-344 rats administered i.v. in a multiple-dose regimen", *Proceedings of the American Association for Cancer Research*, vol. 38, #2073, pp. 309 (1997).

Moore, B.M. et al., "The NMR model of an ecteinascidin 743-DNA adduct", *Proceedings of the American Association for Cancer Research*, vol. 38, #2105, pp. 314 (1997).

Nakagawa, Masako et al., "Total Synthesis of (-)-Eudistomin L and (-)-Debromoeudistomin L", *Journal of the American Chemical Society*, vol. 111, No. 7, pp. 2721-2722 (1989).

Parulekar, A.H. et al., "Bioactivity and Chemical Ecology of Some Interdial Animals", *Bioactivity and Chemical Ecology*, pp. 29-35.

Pommier, Yves et al., "DNA Sequence- and Structure-Selective Alkylation of Guanine N2 in the DNA Minor Groove by Ecteinascidin 743, a Potent Antitumor Compound from the Caribbean Tunicate Ecteinascidia Turbinata", *Biochemistry*, vol. 35, pp. 13303-13309 (1996).

Pretsch et al., *Tables of Spectral Data for Structure Determination of Organic Compounds*, pp. H125 (1983).

Reid, Joel M. et al., "Preclinical pharmacology of ecteinascidin 729, a marine natural product with potent antitumor activity", *Cancer Chemotherapy and Pharmacology*, vol. 38, No. 4, pp. 329-334 (1996).

Remers, William A., "Saframycins, Renieramycins, and Safracins", *The Chemistry of Antitumor Antibiotics*, vol. 2, pp. 93-119 (1988).

Rinehart et al., "Novel Bioactive Natural Products from Marine Organisms", *Topics in Pharmaceutical Sciences 1989*, pp. 613-626, D.D. Breimer, D.J.A. Cromwelin, K.K. Midha, Eds., Amsterdam Medical Press B. V. Noordwijk, The Netherlands (1989).

Rinehart, Kenneth L. et al., "Applications of High-Resolution Tandem FAB Mass Spectrometry", *Biological Mass Spectrometry*, eds. Burlingame et al., Elsevier Amsterdam, pp. 233-258 (1990).

Rinehart, Kenneth L. et al., "Biologically active natural products", *Pure and Applied Chemistry*, vol. 62, No. 7, pp. 1277-1280 (1990).

Rinehart, Kenneth L. et al., "Bioactive Compounds from Aquatic and Terrestrial Sources", *Journal of Natural Products*, vol. 53, No. 4, pp. 771-792 (1990).

Rinehart, Kenneth L., "Antitumor Compounds from Tunicates", *Medicinal Research Reviews*, vol. 20, No. 1, pp. 1-27 (2000).

Rinehart, Kenneth L. et al., "Ecteinascidins 729, 743, 759A, 759B, and 770: Potent Antitumor Agents from the Caribbean Tunicate Exteinascidia Turbinata", *The Journal of Organic Chemistry*, vol. 55, No. 15, pp. 4512-4515 (1990).

Saito, Naoki et al., "Synthesis of Saframycins. 3. Preparation of a Key Tricyclic Lactam Intermediate to Saframycin A", *The Journal of Organic Chemistry*, vol. 54, No. 22, pp. 5391-5395 (1989).

Sakai, Ryuichi et al., "Ecteinascidins: Putative Biosynthetic Precursors and Absolute Stereochemistry", *Journal of the American Chemical Society*, vol. 118, No. 38, pp. 9017-9023 (1996).

Sakai, Ryuichi et al., "Additional antitumor ecteinascidins from a Caribbean tunicate: Crystal structures and activities in vivo", *Proceedings of the National Academy of Sciences*, vol. 89, No. 23, pp. 11456-11460 (1992).

Shamma, Maurice et al., *Carbon-13 NMR Shift Assignments of Amines and Alkaloids*, pp. 206 (1979).

Still, W. Clark et al., "Rapid Chromatographic Technique for Preparative Separations with Moderate Resolution", *Journal of Organic Chemistry*, vol. 43, No. 14, pp. 2923-2925 (1978).

Takahaski, Katsuhiro, "New Antibiotics, Saframycins A, B, C, D and E", *The Journal of Antibiotics*, vol. XXX, No. 11, pp. 1015-1018 (1977).

Takahaski, Katsuhiro et al., "Microbial Conversion of Saframycin A to 25-Dihydrosaframycin A and 21-Decyano-25-Dihydrosaframycin A (25-Dihydrosaframycin B) and Their Biological Activities", *The Journal of Antibiotics*, vol. XXXV, No. 2, pp. 196-202 (1982).

Trowitzsch-Kienast, Wolfram et al., "Isolierung und Strukturaufklarung der Saframycine Mx 1 und Mx 2, neue antitumor-aktive Antibiotika aus Myxococcus xanthus", *Liebigs Ann. Chem.*, vol. XXXV, pp. 475-481 (1988).

Witten, Jane L. et al., "Structures of Two Cockroach Neuropeptides Assigned by Fast Atom bombardment Mass Spectrometry", *Biochemical and Biophysical Research Communications*, vol. 124, No. 2, pp. 350-358 (1984).

Wright, Amy E. et al., "Antitumor Tetrahydroisoquinoline Alkaloids from the Colonial Ascidian Ecteinascidia Turbinata", *The Journal of Organic Chemistry*, vol. 55, No. 15, pp. 4508-4512 (1990).

Yazawa, Katsukiyo et al., "Bioconversions of Saframycin A Specific to some Genera of Actinomycetes", *The Journal of Antibiotics*, vol. XXXV, No. 7, pp. 915-917 (1982).

Yazawa, Katsukiyo et al., "Isolation and Structural Elucidation of New Saframycins Y3, Yd-1, Yd-2, Ad-1, Y2b and Y2b-d", *The Journal of Antibiotics*, vol. XXXIX, No. 12, pp. 1639-1650 (1986).

Zimijewski, Milton J., Jr. et al., "The in vitro Interaction of Naphthyridinomycin with Deoxyribonucleic Acids", *Chemico-Biological Interactions*, vol. 52, No. 3, pp. 361-375 (1985).

Kania, "The First Enantioselective Total Synthesis of Dolabellatrienone and Ecteinascidin 743", Harvard University, Sep. 1997, pp. 1-225.

* cited by examiner

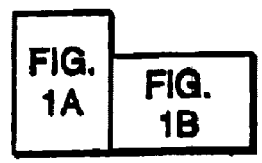

FIG. 1

MORALES, KLR, ETH-SIOH-1 IN CDC13

EXPL S3PUL

| SAMPLE | | DEC. & VT | |
|---|---|---|---|
| DATE | FEB 27 98 | DFRQ | 499.699 |
| SOLVENT | CDC 13 | DN | HL |
| FILE | EXP | DPWR | 20 |
| ACQUISITION | | DOF | 6 |
| STFRQ | 499.699 | DM | NNN |
| TN | 111 | DMM | C |
| AT | 3.277 | DMF | 200 |
| NP | 39296 | DSEQ | |
| SW | 5996.1 | DRES | 1.0 |
| FB | 3400 | HOMO | N |
| BS | 16 | DEC2 | |
| TPWR | 63 | DFRQ2 | 0 |
| PW | 4.7 | DN2 | |
| DL | 0 | DPWR2 | 1 |
| TOF | 0 | DOF2 | 0 |
| NL | 400 | DM2 | N |
| CT | 160 | DMM2 | C |
| ALOCK | N | DMF2 | 200 |
| GAIN | NOT USED | DSEQ2 | |
| FLAGS | | DRES2 | 1.0 |
| 11 | N | HOMO2 | N |
| LN | N | PROCESSING | |
| DP | Y | 16 | 6.30 |
| HS | NN | WTFILE | |
| DISPLAY | | PROC | FT |
| SP | -138.2 | FN | NOT USED |
| WP | 5133.1 | MATH | R |
| VS | 8848 | | |
| SC | 0 | WERR | |
| WC | 250 | WEXP | |
| NIMM | 20.53 | WBS | |
| LS | 33.57 | WNT | |
| RFL | 4131.0 | | |
| RFP | 3627.8 | | |
| TH | 7 | | |
| INS | 1.000 | | |
| NM | PH | | |

FIG. 1A

ESI MASS SPECTRUM OF ETM 775 (NEGATIVE MODE).

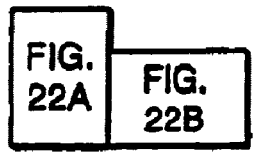

FIG. 22

MORALES, KLR, MZ IN CD3OD

EXPL  S2PUL

| SAMPLE | | DEC. & VT | |
|---|---|---|---|
| DATE | MAR 17 98 | DFRQ | 499.701 |
| SOLVENT | METHANOL | DN | H1 |
| FILE | EXP | DPWR | 20 |
| ACQUISITION | | DOF | 0 |
| STFRQ | 499.701 | DM | NNN |
| TN | 111 | DMM | C |
| AT | 4.003 | DMF | 200 |
| NP | 48000 | DSEQ | |
| SW | 5996.1 | DRES | 1.0 |
| FB | 3400 | HOMO | N |
| BS | 16 | DEC2 | |
| TPWR | 63 | DFRQ2 | 0 |
| PW | 4.5 | DN2 | |
| DL | 0 | DPWR2 | 1 |
| TOF | 0 | DOF2 | 0 |
| NT | 3000 | DM2 | N |
| CT | 1044 | DMM2 | C |
| ALOCK | N | DMF2 | 200 |
| GAIN | NOT USED | DSEQ2 | |
| FLAGS | | DRES2 | 1.0 |
| Il | N | HOMO2 | N |
| LN | N | PROCESSING | |
| DP | Y | LB | 0.30 |
| HS | NN | WTFILE | |
| DISPLAY | | PROC | FT |
| SP | 0.1 | FN | NOT USED |
| WP | 4997.0 | MATH | F |
| VS | 31752 | | |
| SC | 0 | WERR | |
| WC | 250 | WEXP | |
| HZMM | 19.99 | WBS | |
| LS | 33.57 | WNT | |
| RFL | 2154.5 | | |
| RFP | 1649.0 | | |
| TH | 7 | | |
| INS | 1.000 | | |
| NM | PH | | |

FIG. 22A

METABOLITES OF ECTEINASCIDIN 743

CROSS-REFERENCE TO RELATED APPLICATIONS

This application is a continuation of U.S. application Ser. No. 09/971,852, filed on Oct. 3, 2001, now U.S. Pat. No. 6,867,334 which is a continuation of U.S. application Ser. No, 09/309,947, filed on May 11, 1999, now U.S. Pat. No. 6,316,214 which claims the benefit of U.S. Provisional Application Ser. No. 60/085,024, filed May 11, 1998. The contents of these prior applications are incorporated herein by reference in their entireties.

BACKGROUND OF THE INVENTION

The ecteinascidins (herein abbreviated Et or Et's) are exceedingly potent antitumor agents isolated from the marine tunicate *Ecteinascidia turbinata*. In particular, Et's 729, 743 and 722 have demonstrated promising efficacy in vivo, including activity against P388 murine leukemia, B16 melanoma, Lewis lung carcinoma, and several human tumor xenograft models in mice.

The isolation and characterization of natural Et 743 is taught in U.S. Pat. No. 5,089,273 which is hereby incorporated herein by reference. The preparation of synthetic Et 743 is taught in U.S. Pat. No. 5,721,362, which is hereby incorporated herein by reference.

The antitumor activities of ecteinascidin compounds, particularly Et 729 and Et 743 are well documented in the scientific literature. See for example, Goldwasser et al., *Proceedings of the American Association for Cancer Research*, 39: 598 (1998); Kuffel et al., *Proceedings of the American Association for Cancer Research*, 38: 596 (1997); Moore et al., *Proceedings of the American Association for Cancer Research*, 38: 314 (1997); Mirsalis et al., *Proceedings of the American Association for Cancer Research*, 38: 309 (1997); Reid et al., *Cancer Chemotherapy and Pharmacology*, 38: 329–334 (1996); Faircloth et al., *European Journal of Cancer*, 32A, Supp. 1, pp. S5 (1996); Garcia-Rocha et al., *British Journal of Cancer*, 73: 875–883 (1996); Eckhardt et al., *Proceedings of the American Association for Cancer Research*, 37: 409 (1996); Hendriks et al., *Proceedings of the American Association for Cancer Research*, 37: 389 (1996); the disclosures of which are hereby incorporated herein by reference.

Ecteinascidin 743 (Et 743) has the following structure:

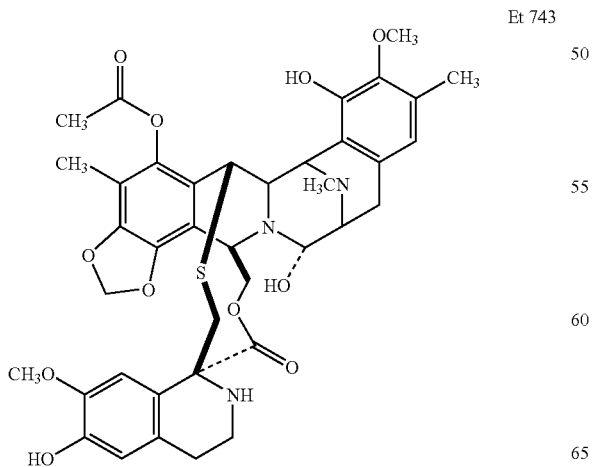

In view of the impressive antitumor activities of this class of compounds, the search continues for related structures that may possess equal or higher levels of antitumor activity. The present invention, which is directed to the isolation and characterization of natural metabolites of Et 743, is a result of these continued studies.

SUMMARY OF THE INVENTION

The purification and structure elucidation of several products of the metabolism of Et 743 by human cytochrome CYP3A4 have been accomplished. These compounds are abbreviated herein as "ETM" followed by a numeric value which represents the approximate molecular weight.

For example, ETM 305 and ETM 775 were isolated from a metabolic mixture obtained from a biochemical study performed by the Analytical Chemistry Department at PharmaMar, Spain. A similar metabolic study carried out by the Mayo Clinic led to the identification of ETM 204. The structures of these ecteinascidin metabolites are as follows:

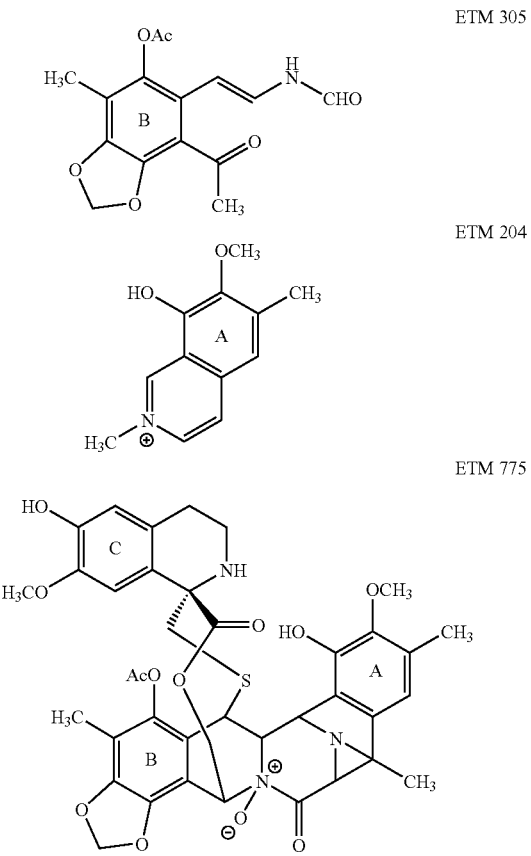

BRIEF DESCRIPTION OF THE DRAWINGS

The present invention may be better understood by reference to the drawings accompanying this specification, wherein.

DETAILED DESCRIPTION OF THE INVENTION

I. Et 743 Metabolic Study

A. Preparation of Metabolic Mixture—ETM:

Et-743 (50 μM) was incubated with 0.4 mg/ml of human lymphoblast-expressed CYP3A4 isoform (Gentest Corporation, Woburn, Mass.) in 0.1 M Tris-HCl buffer (pH 7.4) containing an NADPH generating system (0.4 mM $NADP^+$, 25 mM glucose-6-phosphate, 0.5 U/ml glucose-6-phosphate dehydrogenase and 3.3 mM magnesium chloride). After four (4) hours at 37° C., the reaction was stopped with ice cold acetonitrile and the solids removed by centrifugation (12,000 g, 4 min.). Supernatants were analyzed by HPLC.

B. Purification of ETM 305 and ETM 775

Figure 1B:
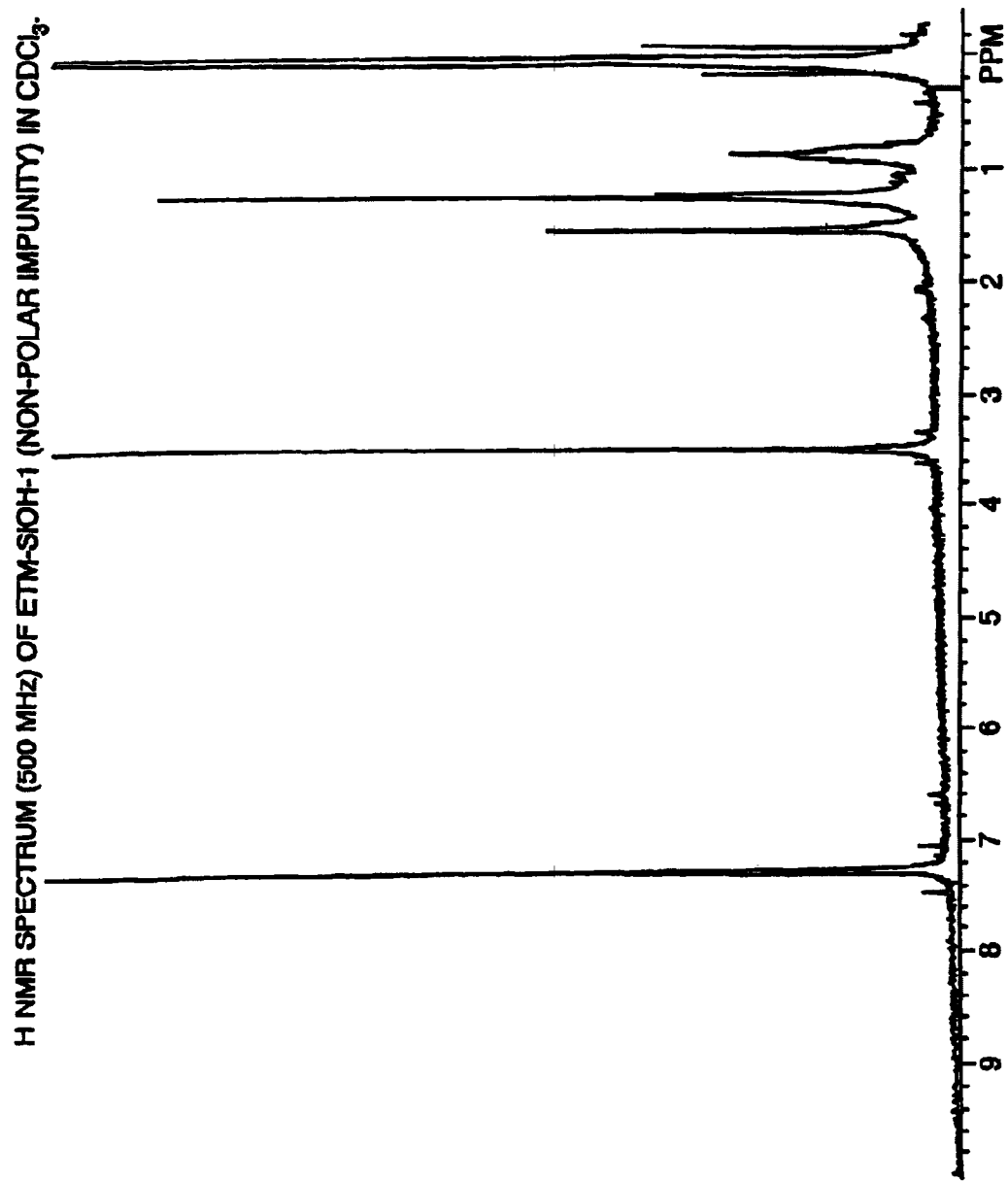
FIG. 1 is the $^1$H NMR spectrum (500 MHz) of ETM-SiOH-1 (non-polar impurity) in CDCl$_3$.

2.6 mg of ETM (generated as in A, above) was dissolved in a small amount of $CHCl_3$ and loaded into a silica gel column (8×100 mm glass column filled with a silica gel/ $CHCl_3$ slurry). First, the column was eluted with $CHCl_3$ followed by $CHCl_3$/MeOH mixtures (98, 96, 94, 92 and 90%). A total of ten test tubes were collected (3 mL each) and combined on the basis of TLC to yield four fractions (Table 1). The less polar and non-cytotoxic fraction (ETM-SiOH-1,2 mg) consisted of a lipid not structurally related to Et 743 as revealed by the $^1$H NMR spectrum (FIG. 1).

Figure 2:
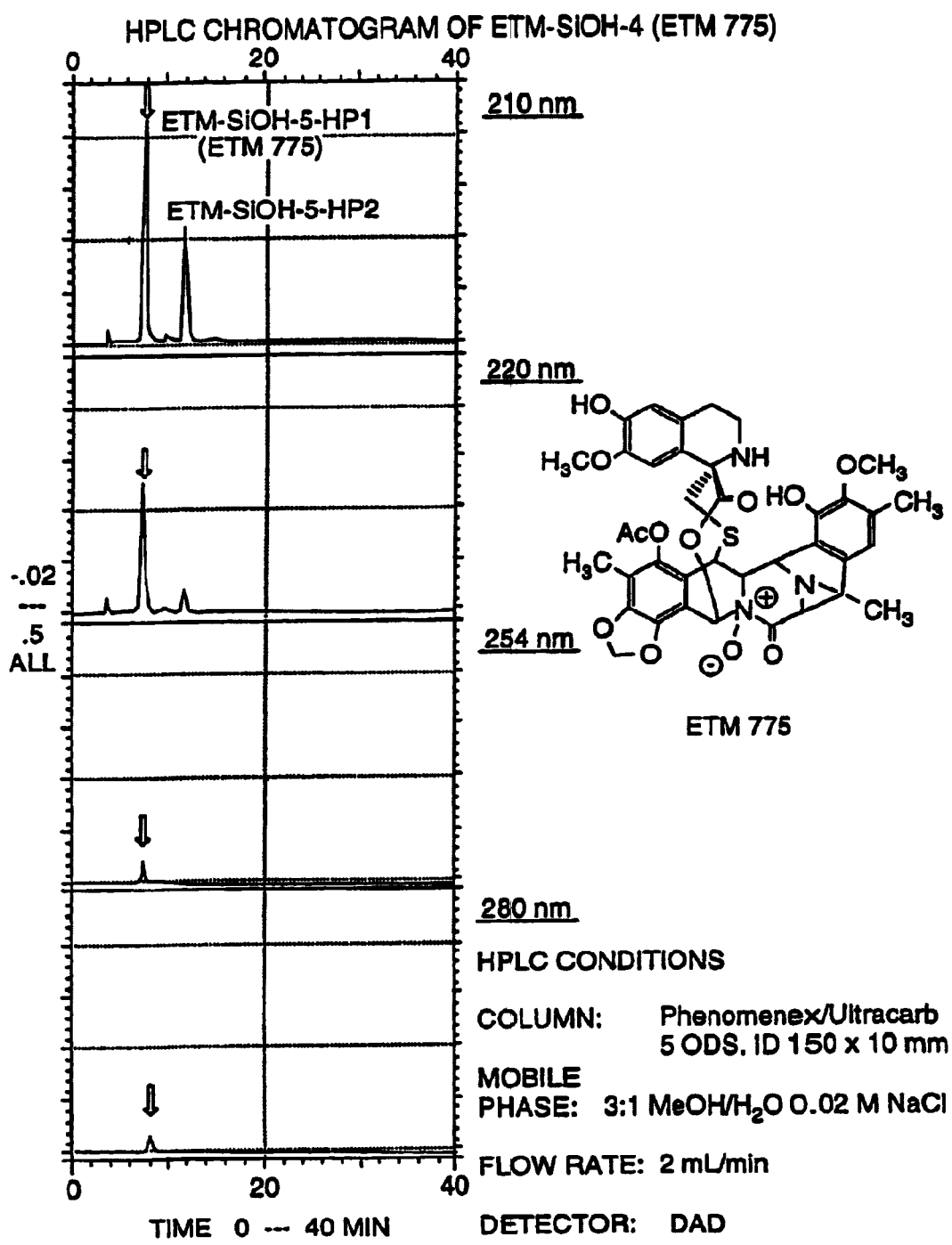
FIG. 2 is the HPLC chromatogram of ETM-SiOH-4 (ETM 775)
Figure 3:
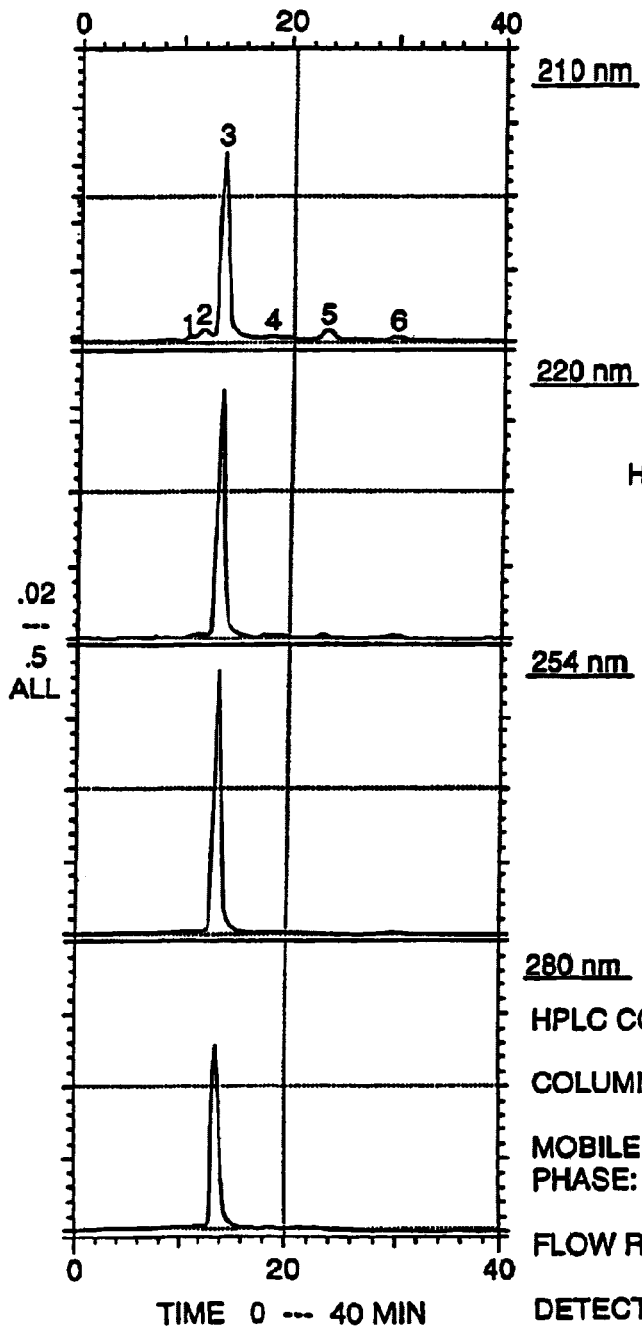
FIG. 3 is the HPLC chromatogram of ETM-SiOH-3 (ETM 305)
Figure 4:
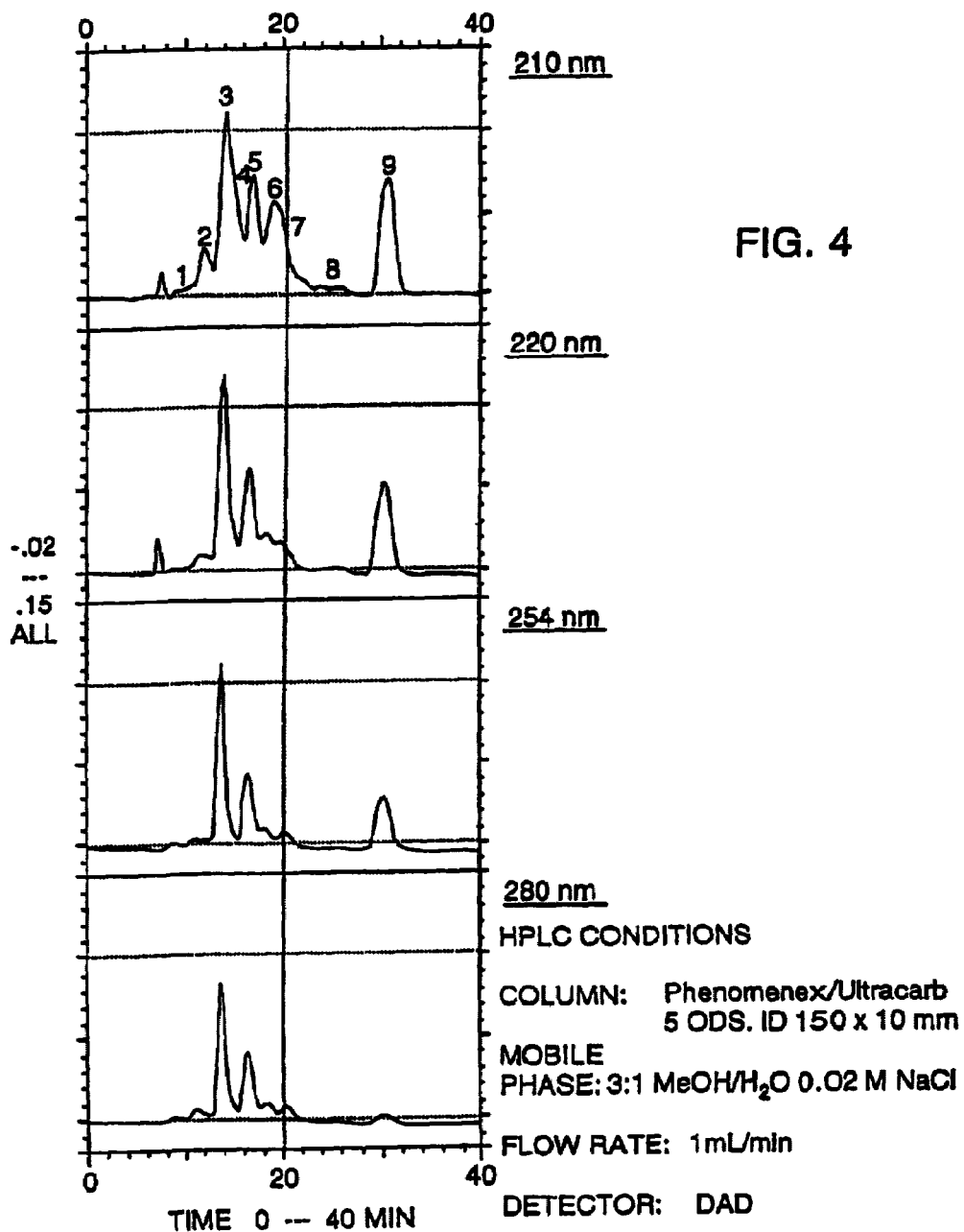
FIG. 4 is the HPLC chromatogram of ETM-SiOH-2 (trace metabolites)

The remaining cytotoxic fractions were further purified by HPLC (Phenomenex-Ultracarb ODS, 10 μm, 10×150 mm, 3:1 MeOH/$H_2O$ 0.02 M NaCl, 1 mL/min., Da Detection: 210, 220, 254 and 280 nm). The most polar fraction (ETM-SiOH-4, 0.2 mg) yield 0.1 mg of ETM 775 (FIG. 2). ETM-SiOH-3 yield 0.3 mg of ETM 305 (FIG. 3), and ETM-SiOH-2 consisted of a complex mixture of trace metabolites (FIG. 4).

TABLE 1

ETM-SiOH fractions: $R_f$, weight and cytoxic activity.

| ID# | Test tube # | $R_f$[a] | Weight | L1210 growth inhibition (%) at 500 ng/mL |
|---|---|---|---|---|
| ETM-SiOH 1 | 1 | 0.9 | 2.0 mg | 0 |
| ETM-SiOH 2 | 2 | 0.5, 0.7 | 0.3 mg | 80[b] |
| ETM-SiOH 3 | 4–5 | 0.5 | 0.4 mg | 30 |
| ETM-SiOH 4 | 6 | 0.3 | 0.2 mg | 3 |

[a]Silica gel TLC using 9:1 $CHCl_3$/MeOH as mobile phase.
[b]30% inhibition at 250 ng.

C. The Structure of ETM 305.

Figure 5:
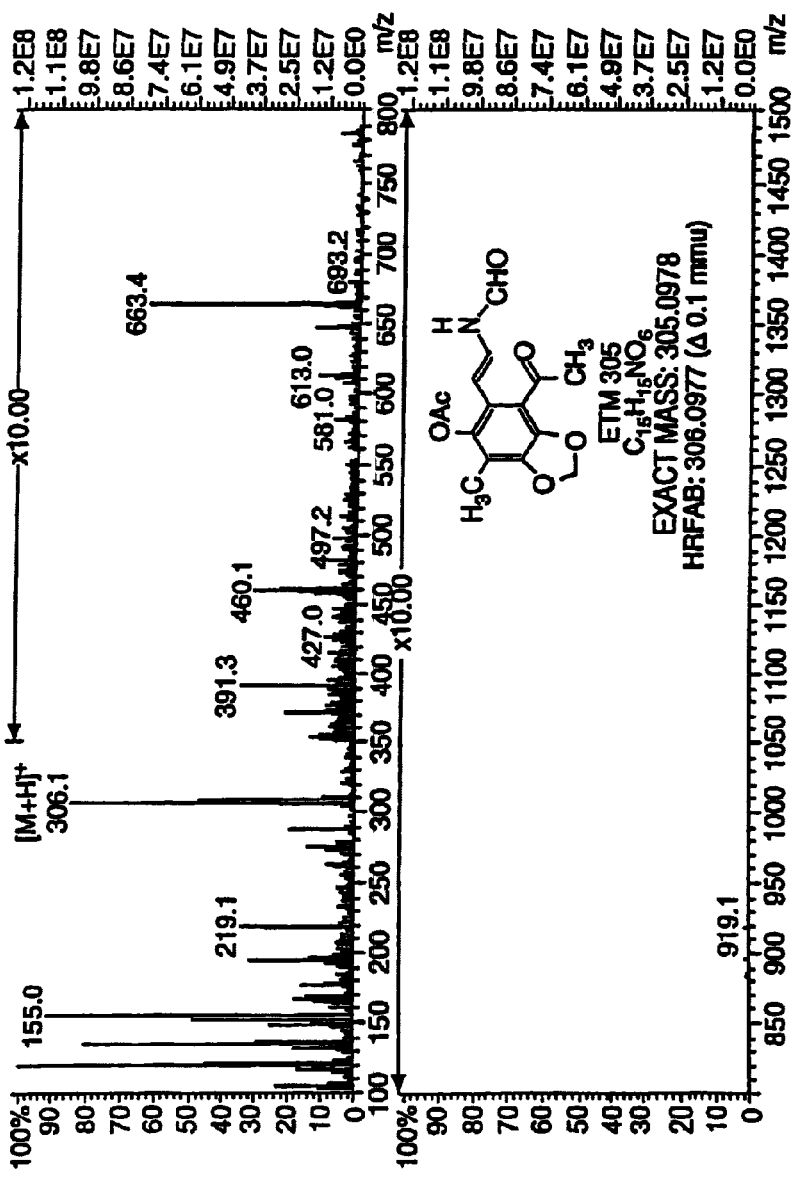
FIG. 5 is the LRFAB mass spectrum of ETM 305 in M.B. (magic bullet[4])
Figure 6:
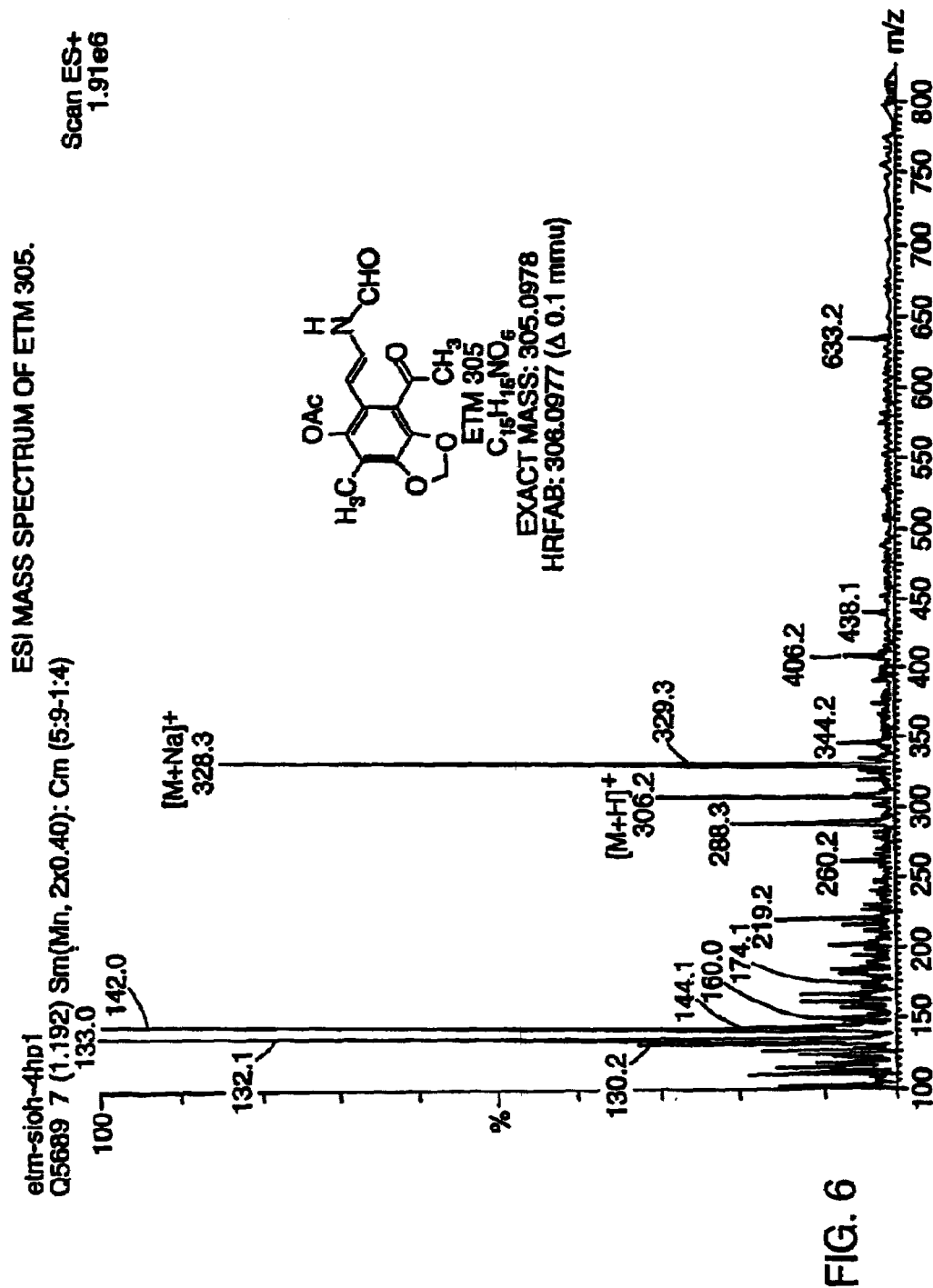
FIG. 6 is the ESI mass spectrum of ETM 305.
Figure 7:
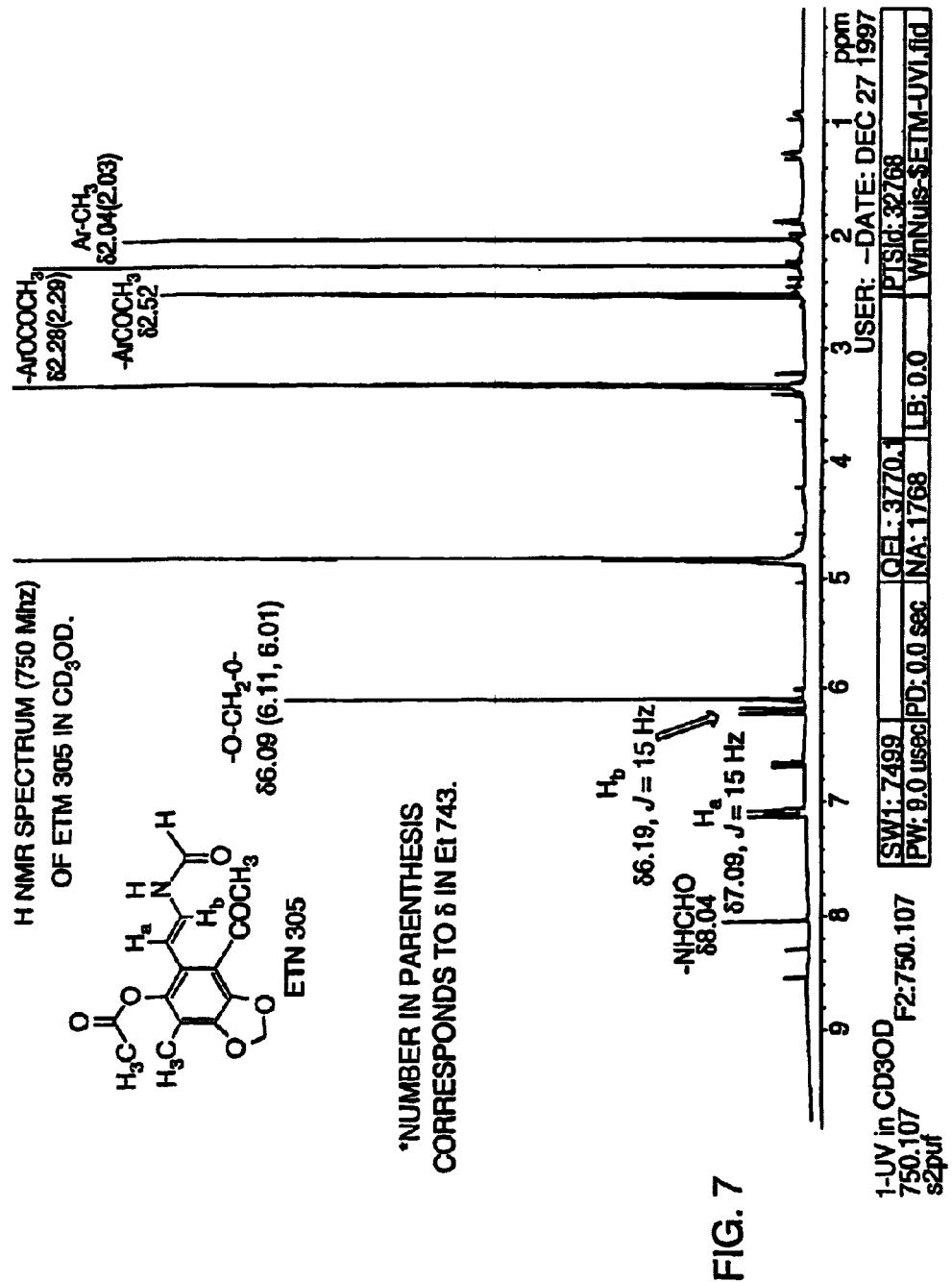
FIG. 7 is the $^1$H NMR spectrum (750 MHz) of ETM 305 in $CD_3OD$.

ETM 305 ($IC_{50}$ 0.2 μm/mL vs L1210 cells) showed a molecular ion at 306.0977 by HRFAB/MS (FIG. 5). This data is in agreement with the molecular formula $C_{15}H_{16}NO_6$ (Δ0.1 mmu). ESI/MS analysis confirmed the molecular weight of ETM 305 (FIG. 6); a molecular ion at m/z 306 was observed together with its sodium adduct (m/z 328). The $^1$H NMR spectrum of ETM 305 (FIG. 7) was very important for the structural assignment. Resonances at δ 2.04, 2.28 and 6.09 were almost identical to those of Me-6 (δ 2.03), —$OCOCH_3$ (δ 2.29) and the dioxy-methylene protons (δ 6.11 and 6.01) in Et 743,[1] respectively.

Figure 8:
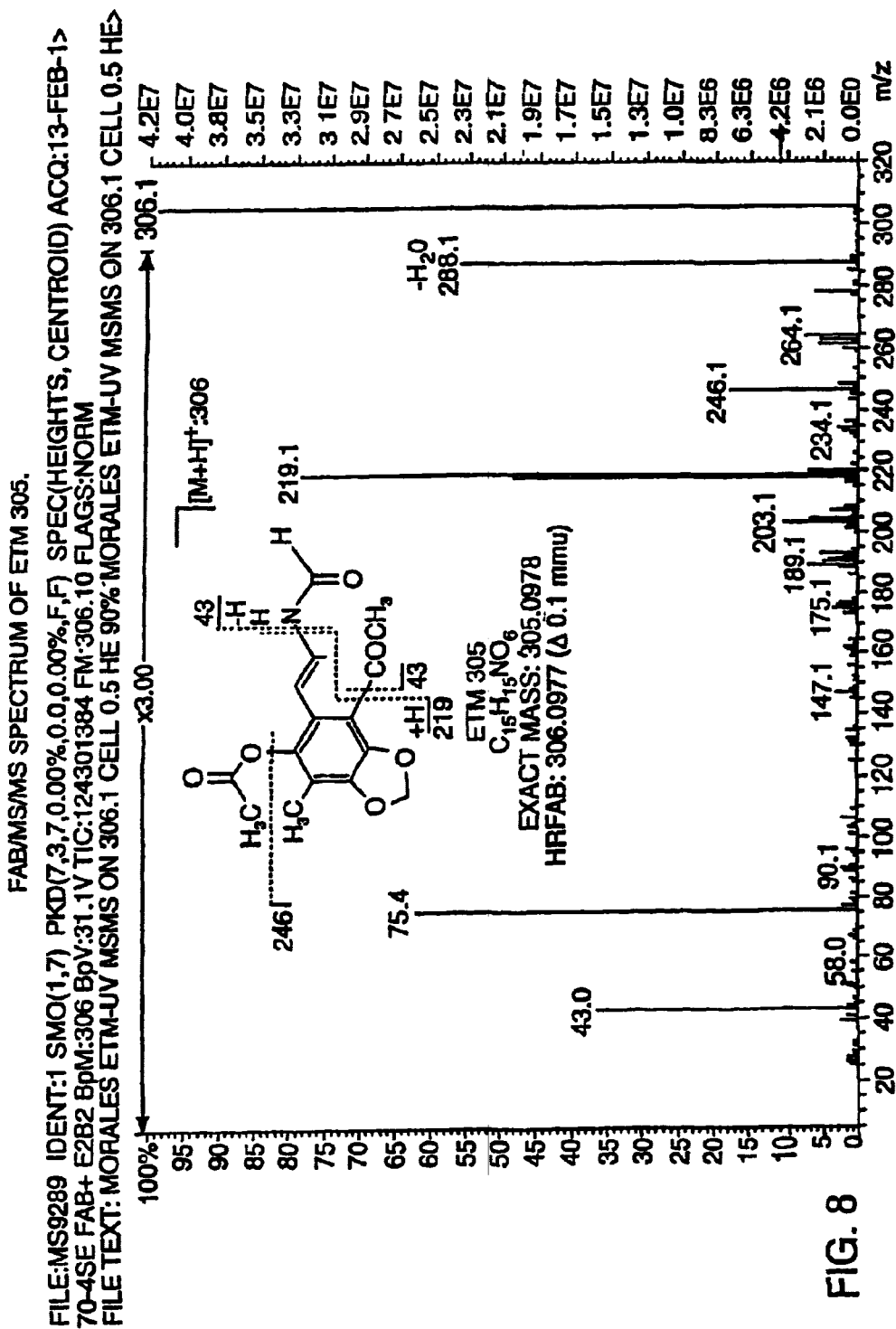
FIG. 8 is the FAB/MS/MS spectrum of ETM 305.
Figure 9:
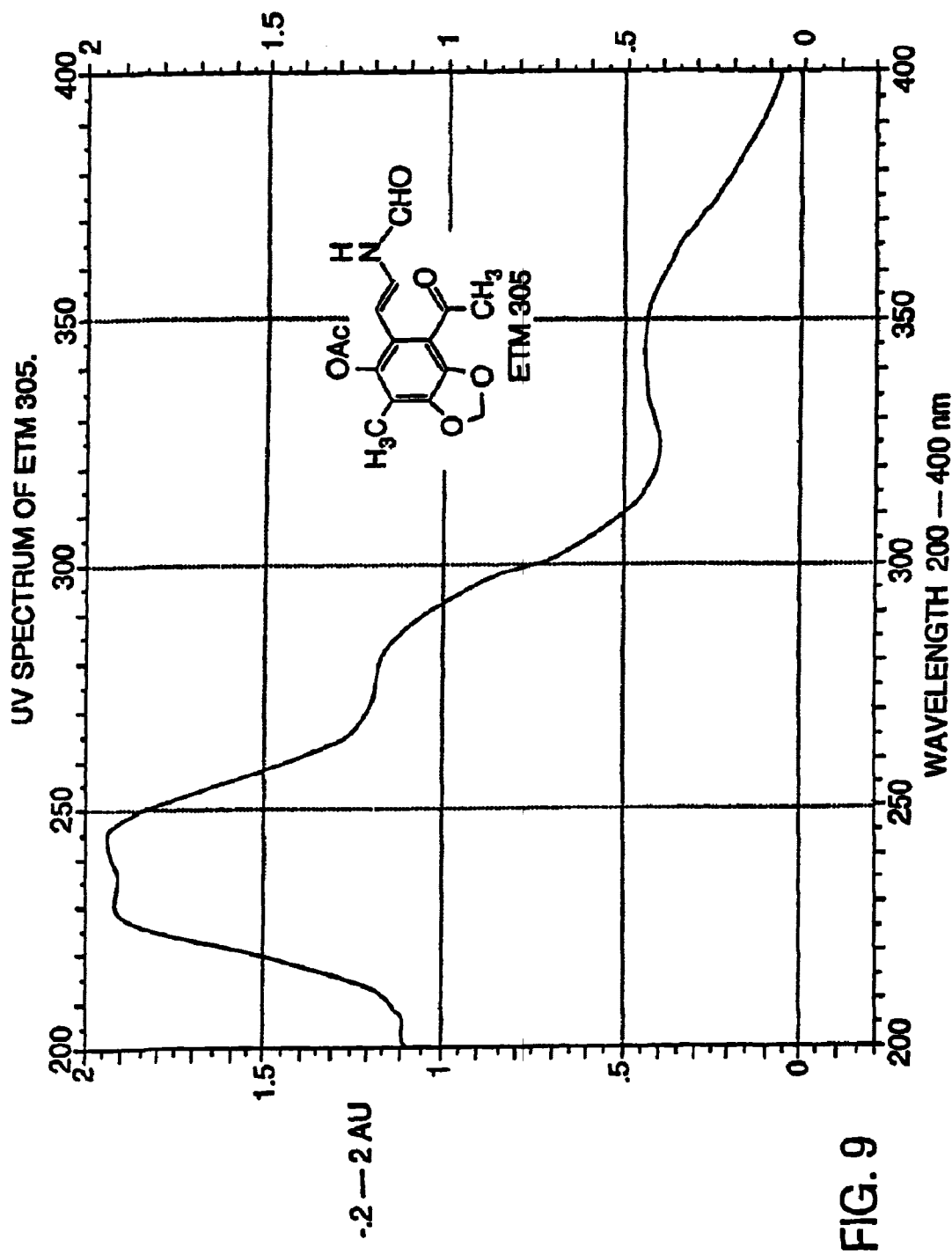
FIG. 9 is the UV spectrum of ETM 305.
Figure 10:
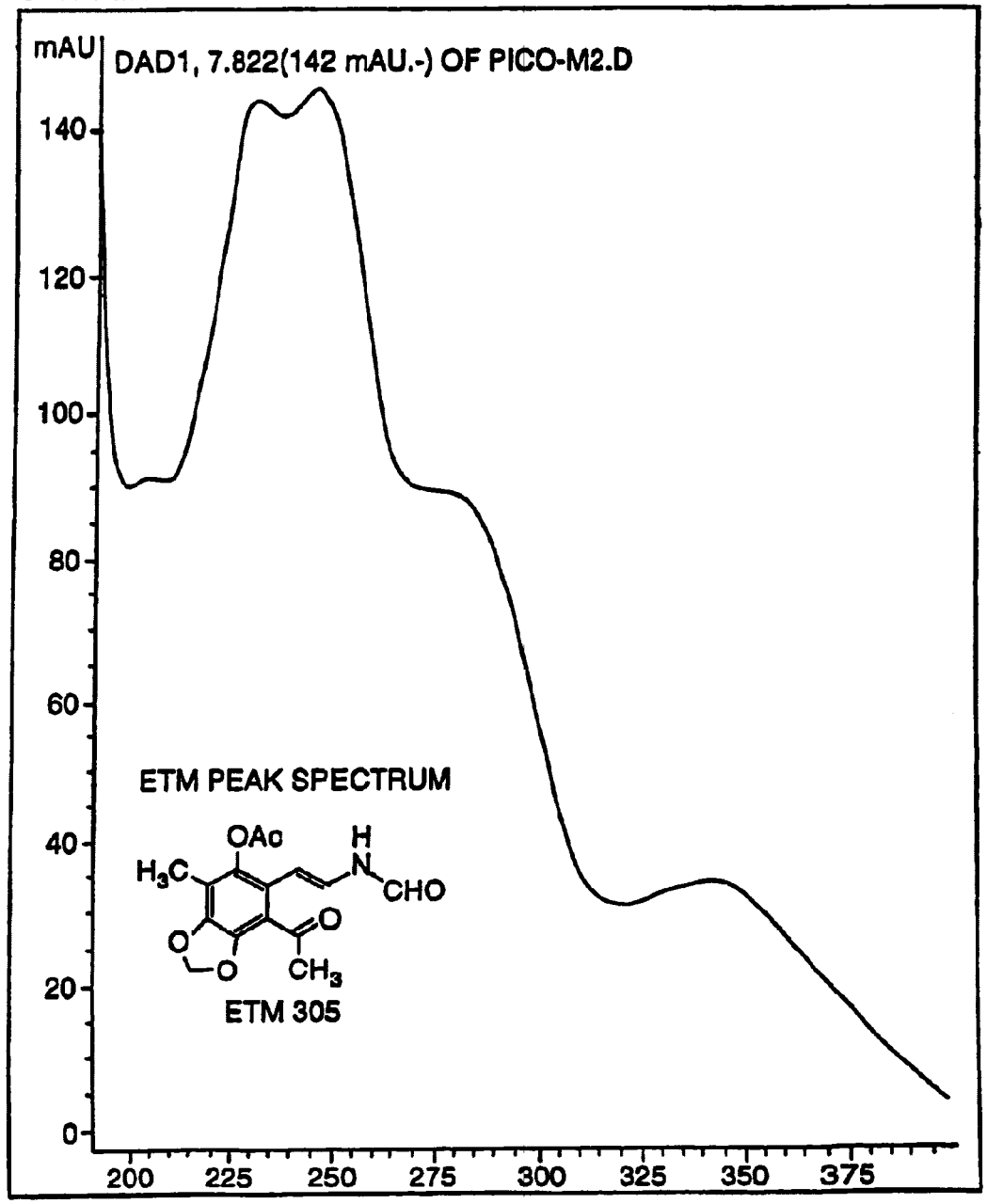
FIG. 10 is the UV spectrum of ETM.

In addition, it was observed resonances corresponding to a —CH=CH—NHCHO unit (δ 7.09, d, 1H, J=15 Hz; δ 6.19, d, 1H, J=15 Hz; δ 8.04, s, 1H),[2] and an additional methyl group (δ 2.52, s, 3H). The chemical shift of this methyl group match pretty well wit that of the methyl group on acetophenone[3] (δ 2.55). It is interesting to note that the $^1$H NMR spectrum of ETM 305 consisted of two sets of resonances (4:1 ratio) due to rotational conformers around the —NH—CHO bond The $^1$H NMR data together with the MS data suggested that ETM 305 had the B-unit aromatic ring system of Et 743 attached to a vinyl-formamide unit and to a methyl ketone as shown in Scheme 1. FAB/MS/MS on m/z 306 supported the proposed structure (FIG. 8).

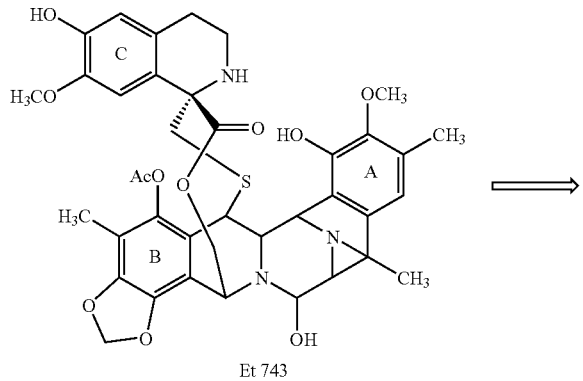

Scheme 1

Et 743

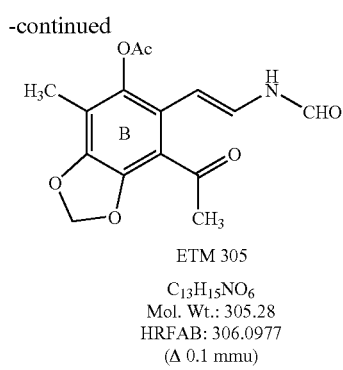

ETM 305
$C_{13}H_{15}NO_6$
Mol. Wt.: 305.28
HRFAB: 306.0977
(Δ 0.1 mmu)

D. The Structure of ETM 775.

Figure 11:
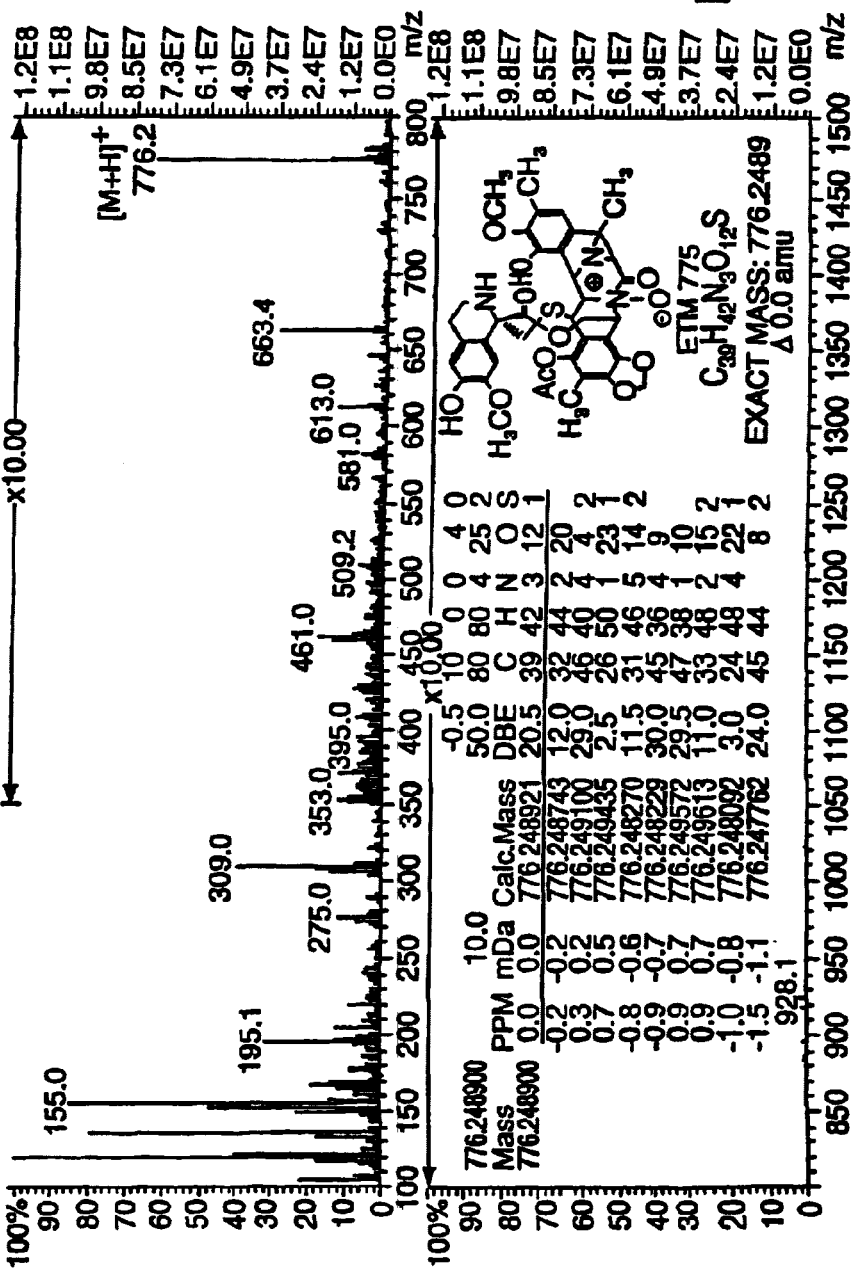
FIG. 11 is the LRFAB mass spectrum of ETM 775 in M.B.
Figure 12:
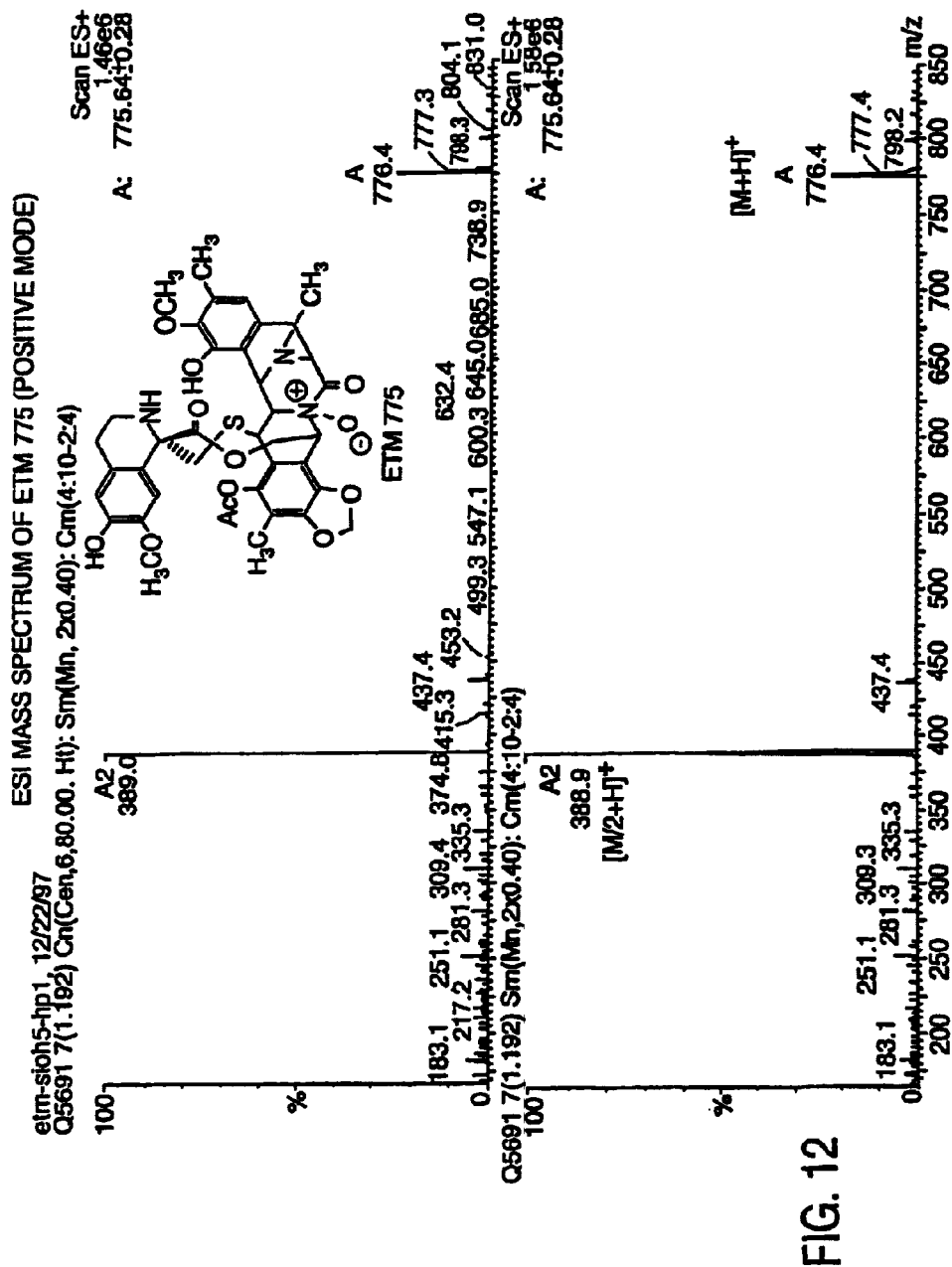
FIG. 12 is the ESI mass spectrum of ETM 775 (positive mode)
Figure 13:
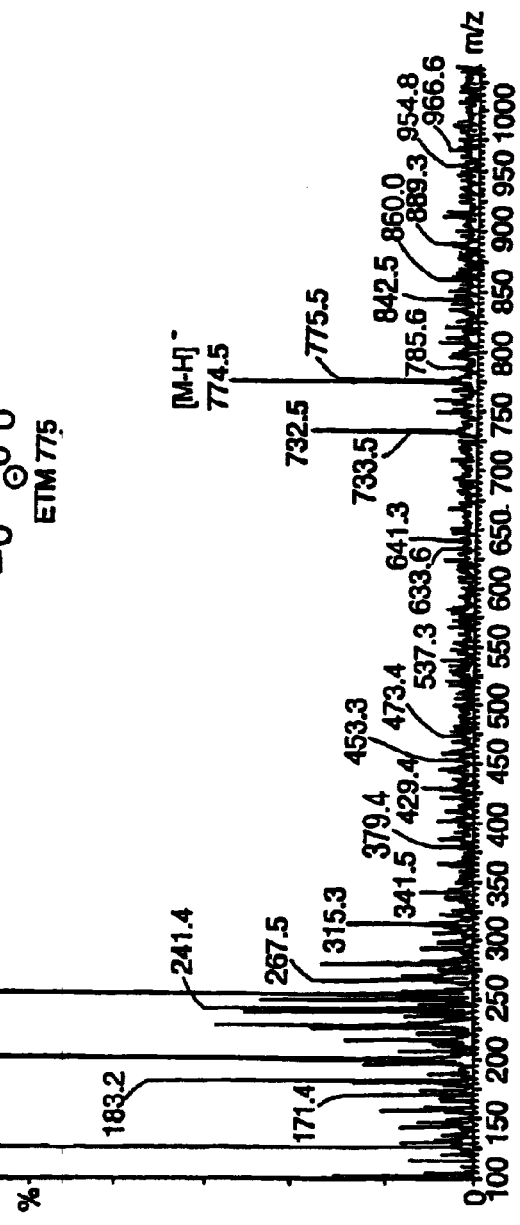
FIG. 13 is the ESI mass spectrum of ETM 775 (negative mode)
Figure 14:
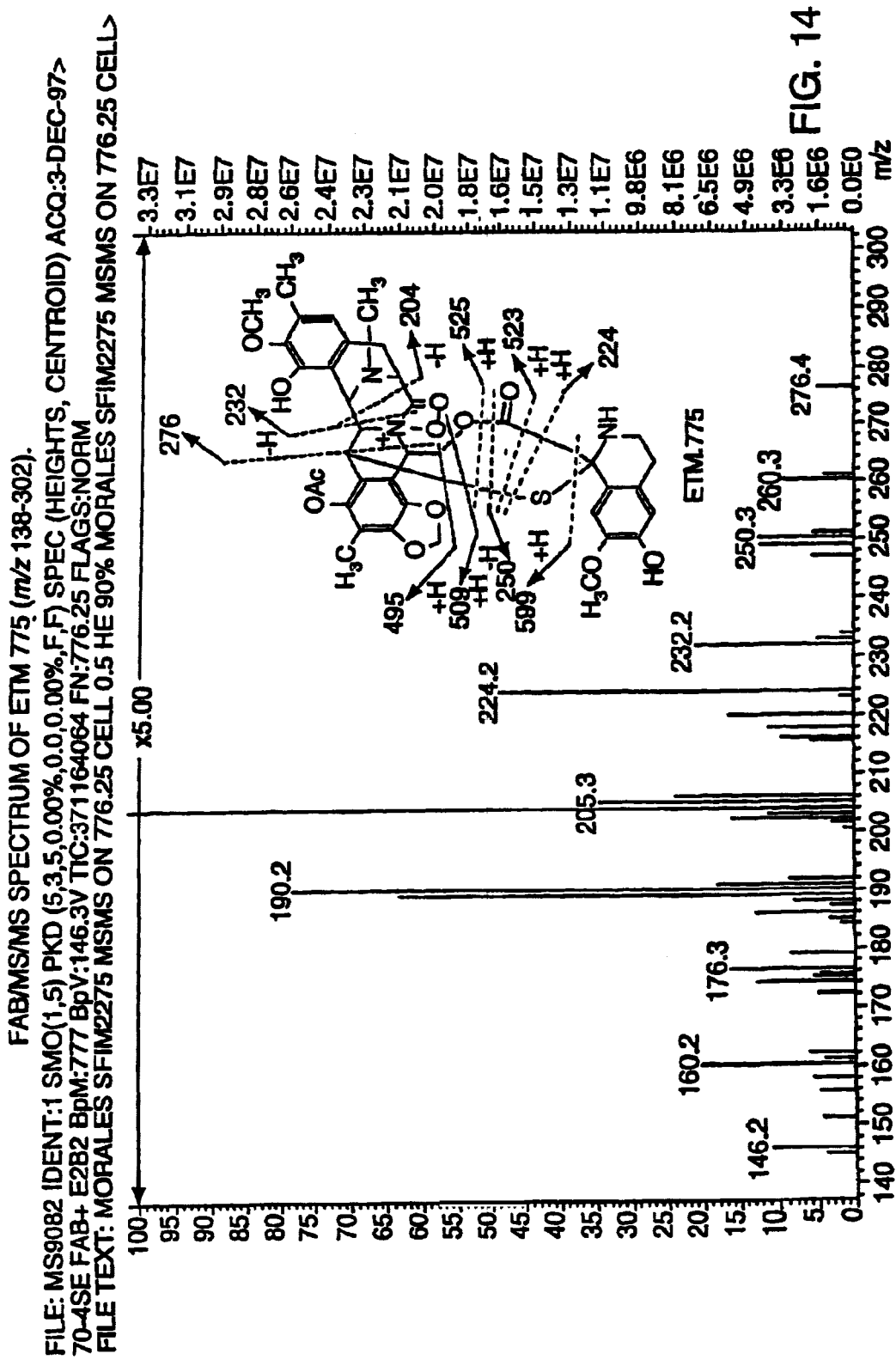
FIG. 14 is the FAB/MS/MS spectrum of ETM 775 (m/z 138–302)
Figure 15:
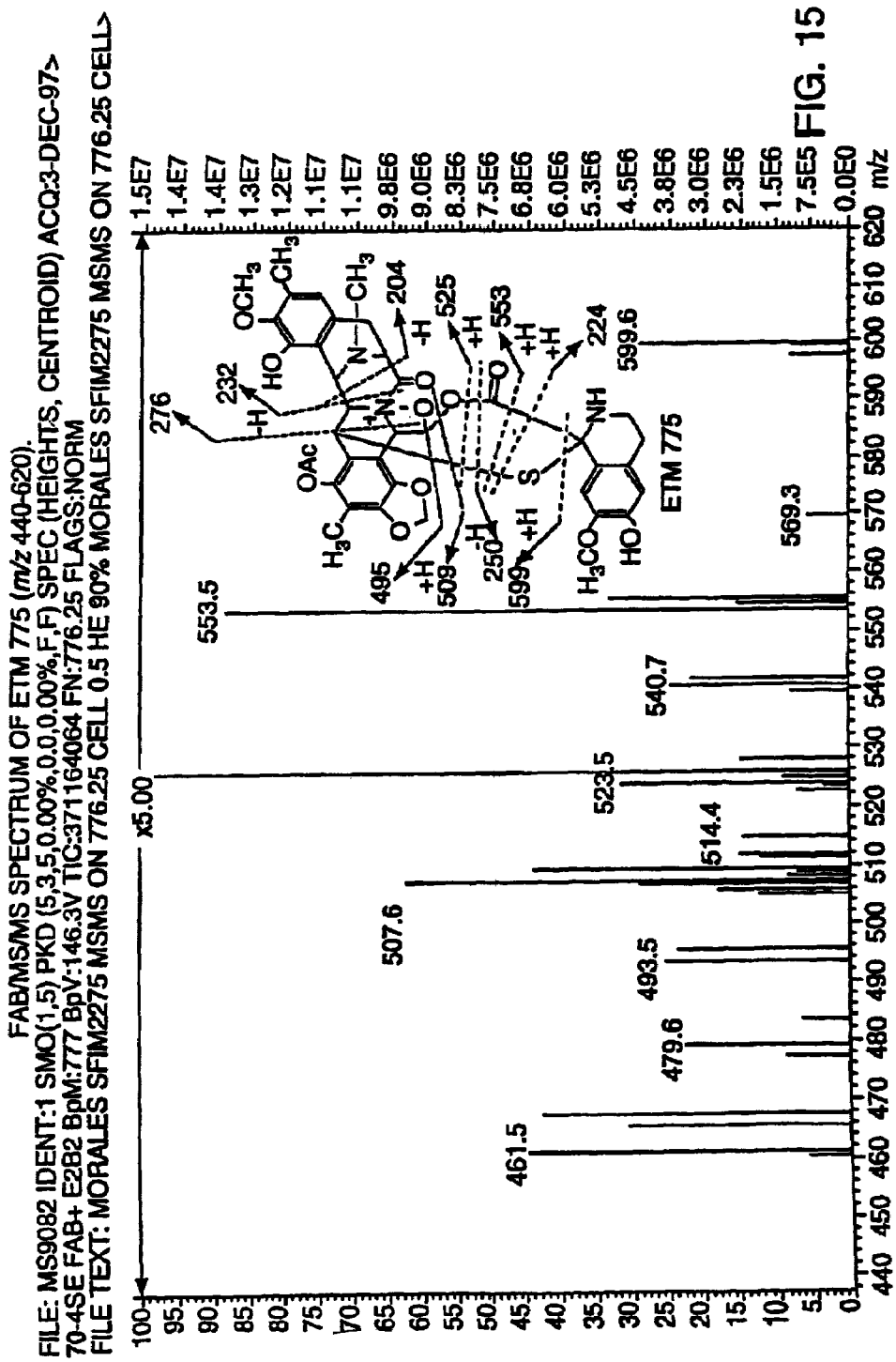
FIG. 15 is the FAB/MS/MS spectrum of ETM 775 (m/z 440–620)
Figure 16:
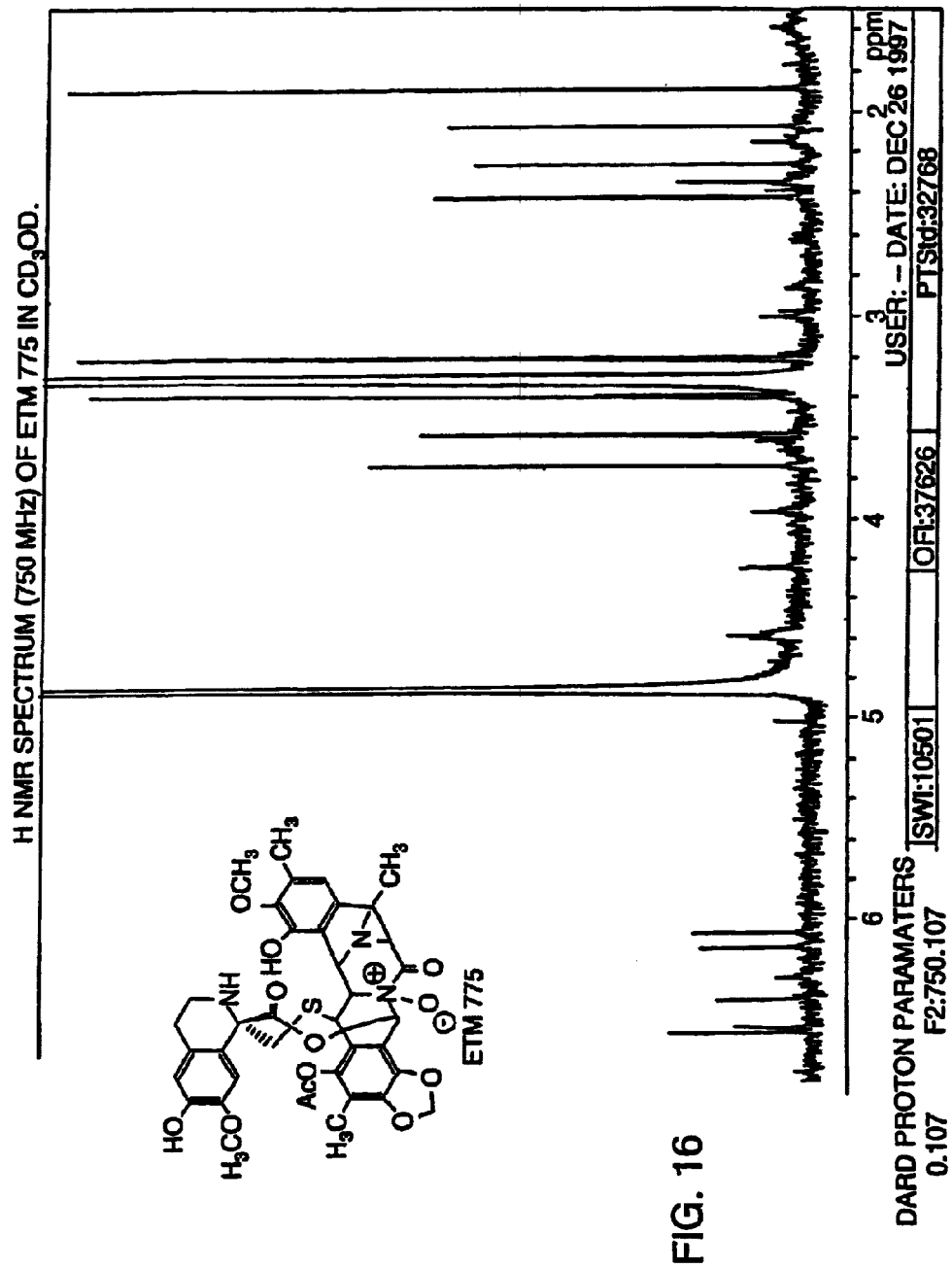
FIG. 16 is the $^1$H NMR spectrum (750 MHz) of ETM 775 in $CD_3OD$.
Figure 17:
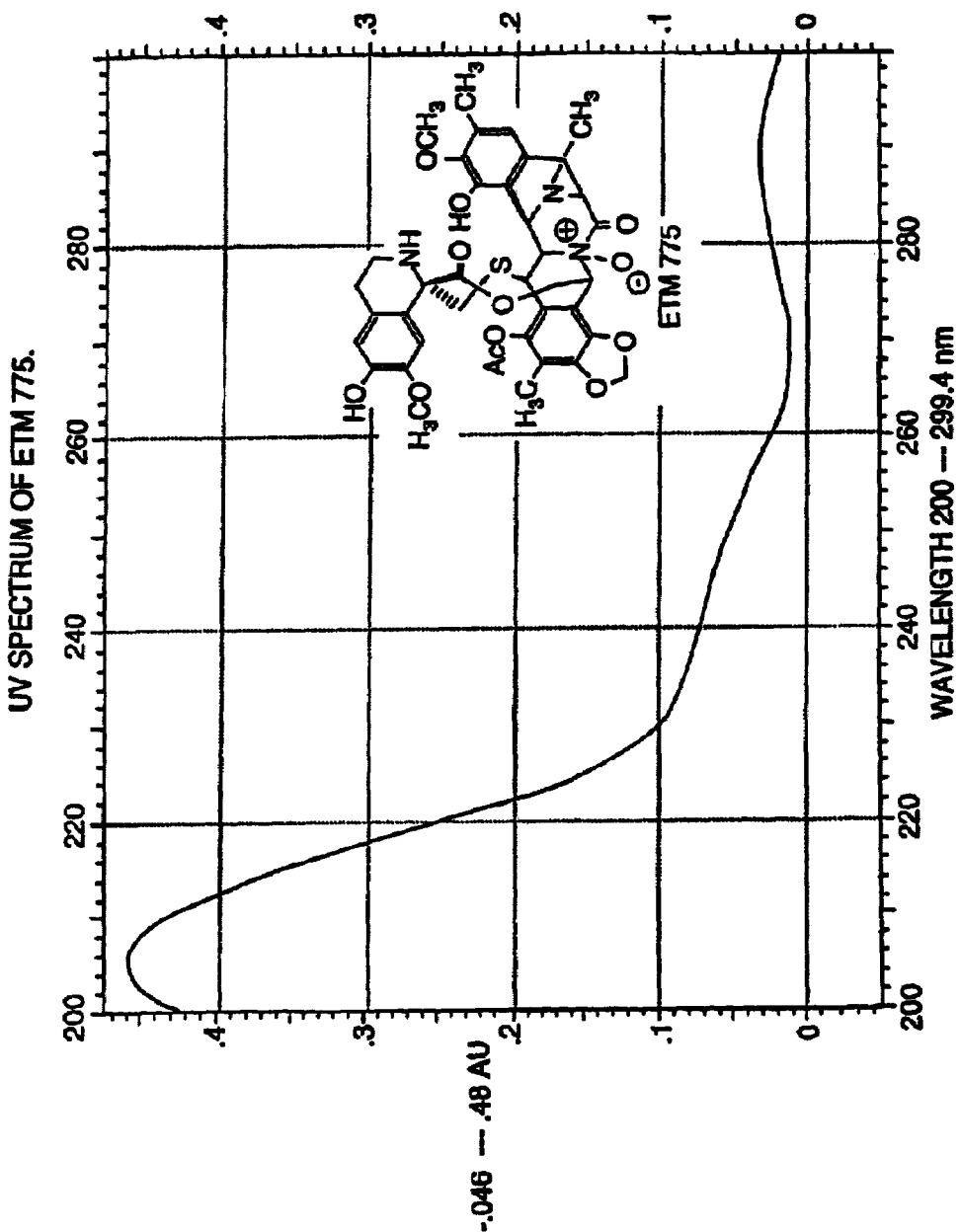
FIG. 17 is the UV spectrum of ETM 775.

ETM 775 ($IC_{50}$ 0.2 μg/mL vs L1210 cells) showed a molecular ion at 776.2489 by HRFAB/MS (FIG. 11). This data is in agreement with the molecular formula $C_{39}H_{42}N_3O_{12}S$ (Δ0.0 mmu) which indicated that ETM 775 is an oxidation product of Et 743. Both, positive and negative mode ESI/MS spectra confirmed the molecular weight of ETM 775 (FIGS. 12 and 13). Because of the limited amount of ETM 775, the structural assignment was carried out mainly by interpretation of its mass spectral data. FABMS/MS on M+H of ETM 775 (m/z 776) was critical in assigning the location of the extra oxygen was located on N-2 in the form of an N-oxide as revealed by peaks at m/z 276 and 260 (276-oxygen). A fragment ion at m/z 232, not observed in Et 743, suggested that the carbinol amine oxygen was oxidized to the amide (Scheme 3). The structures of the A- and C-units in ETM 775 remained intact as revealed by the presence of the characteristic mass spectral peaks at m/z 204 (A-unit), and m/z 224 and 250 (C-unit).[1] Both, the 750 750 Mhz $^1$H NMR (FIG. 16) and the UV (FIG. 17) spectra resembled those of Et 743.[1]

Scheme 2

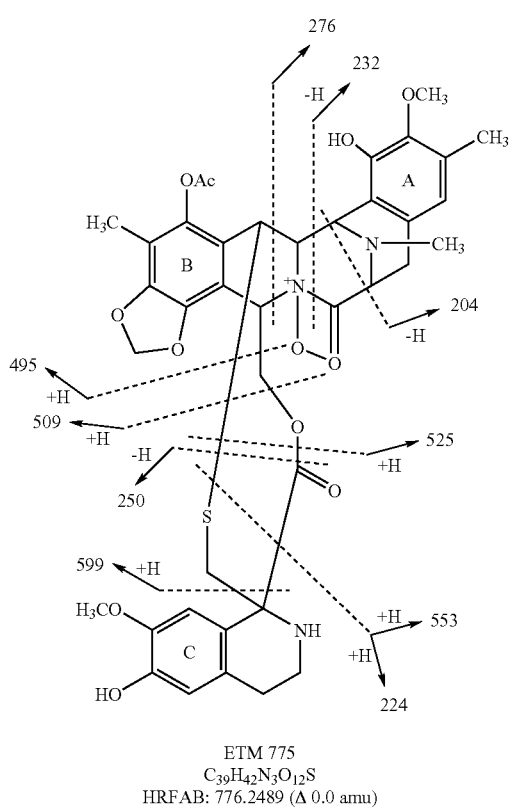

ETM 775
$C_{39}H_{42}N_3O_{12}S$
HRFAB: 776.2489 (Δ 0.0 amu)

II. Et 743—Mayo Metabolic Study

A. M1 metabolite (ETM 305).

Figure 18:
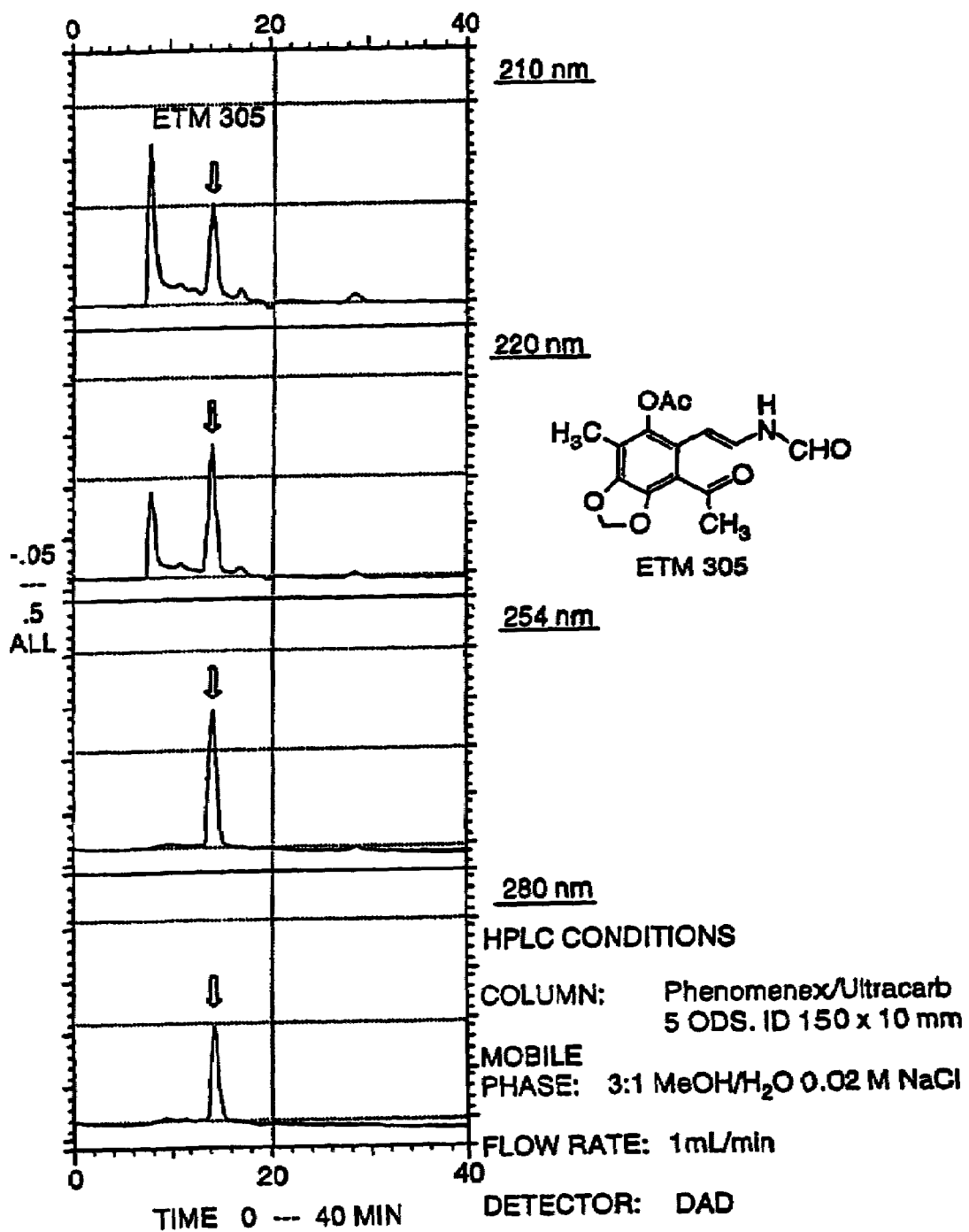
FIG. 18 is the HPLC choromatogram of ETM 305.
Figure 19:
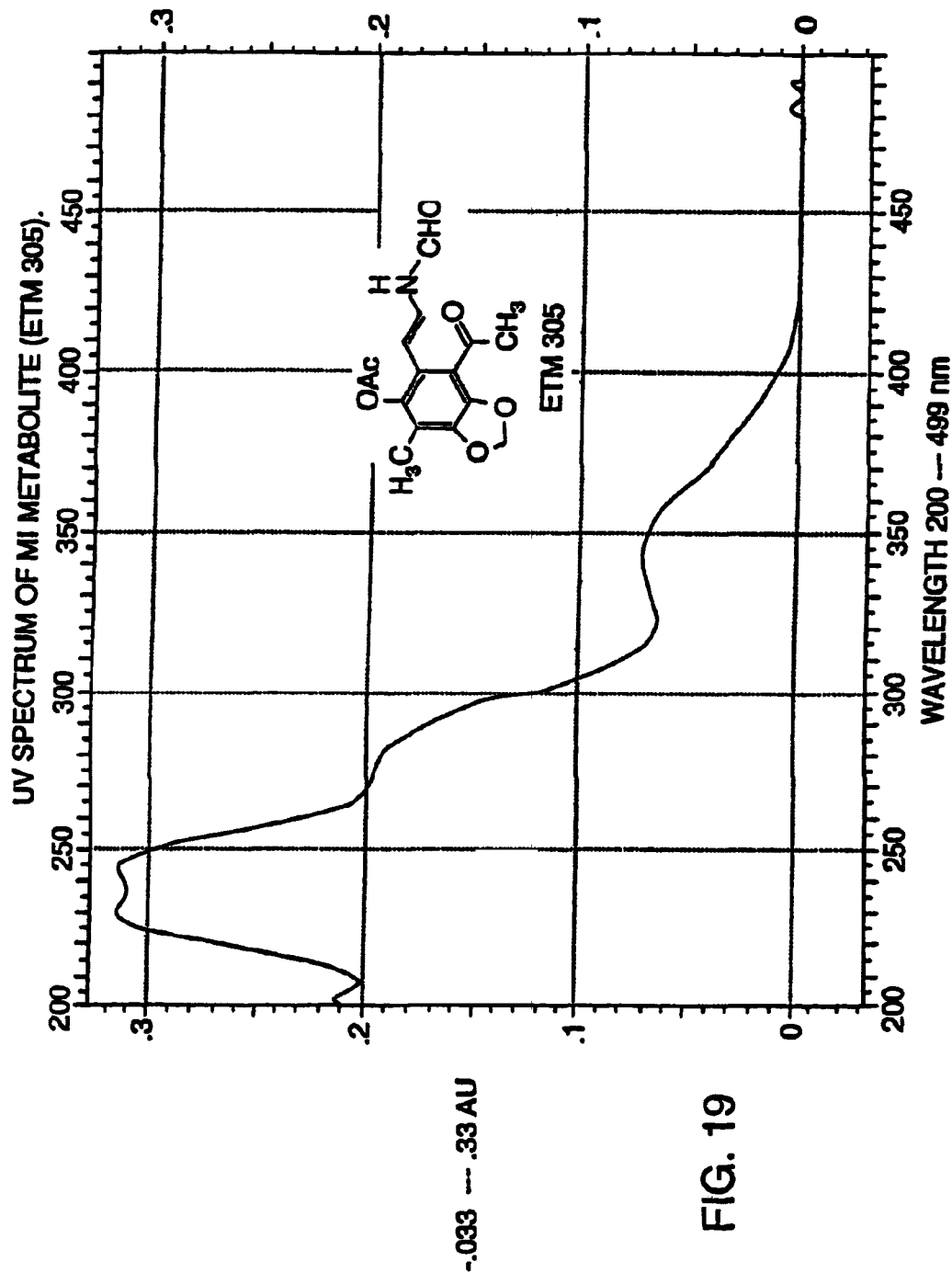
FIG. 19 is the UV spectrum of ETM 305.
Figure 20:
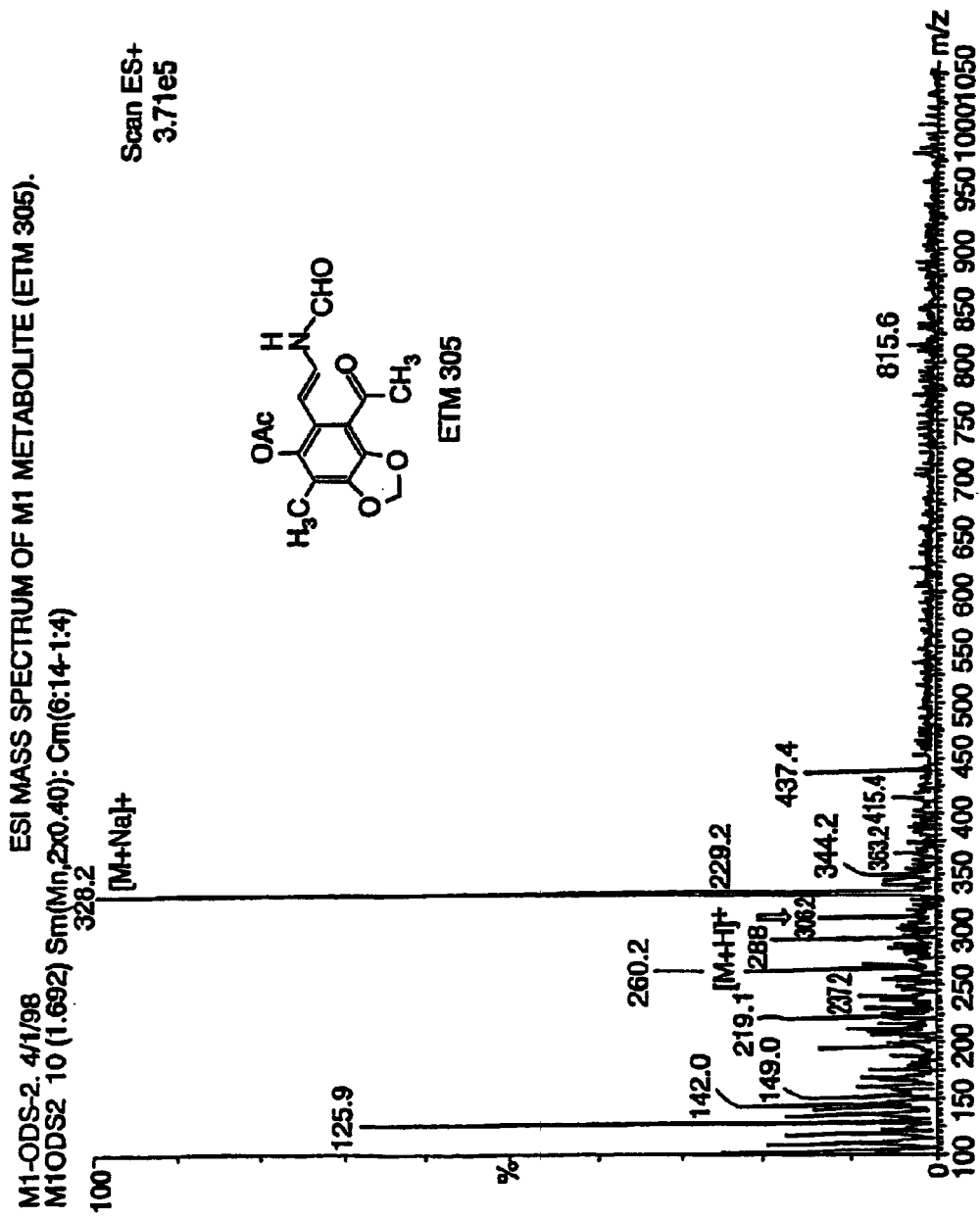
FIG. 20 is the ESI mass spectrum of ETM 305.

The ETM sample was filtered through a C18 sep-pack and the eluant (3:1 MeOH/$H_2O$) concentrated under a nitrogen stream. Purification of the resulting residue by HPLC (same conditions as described above) revealed the presence of a compound with a retention time identical to that of ETM 305 (FIG. 18). Both, the UV (FIG. 19) and ESI/MS (FIG. 20) spectra of M1 were identical to that of ETM 305. Thus, it was concluded that M1 metabolite had the same chemical structure as ETM 305.

B. M2 Metabolite (ETM 204).

The provided sample was filtered through a C18 sep-pack and the eluant (3:1 MeOH/$H_2O$) concentrated under a nitrogen stream and the resulting residue analyzed by FAB/MS, ESI/MS and $^1$H NMR.

C. The Structure of ETM 204 (M2).

Figure 21:
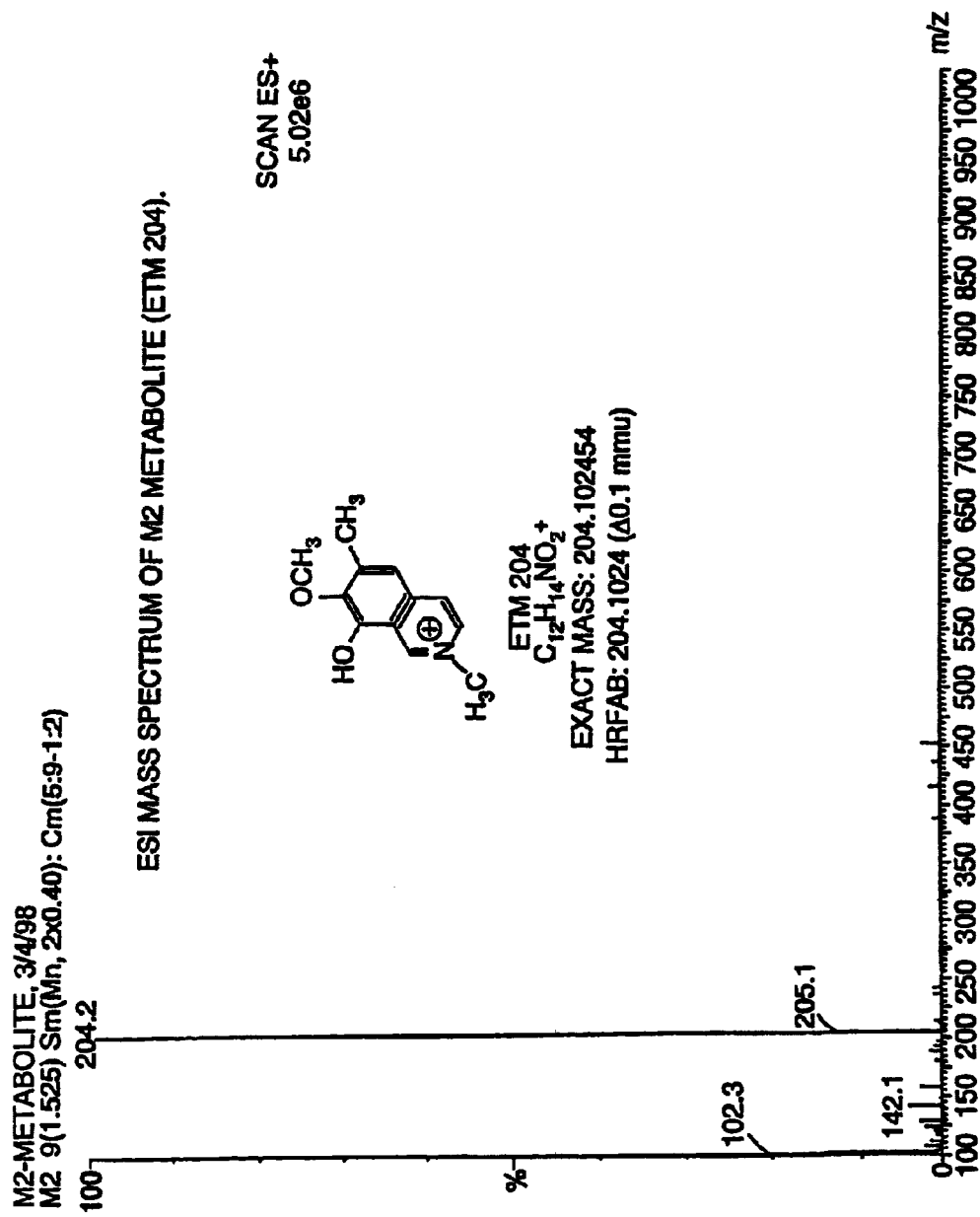
FIG. 21 is the ESI mass spectrum of ETM 204.

ETM 204 showed a molecular ion at 204.1024 by HRFAB/MS. This data is in agreement with the molecular formula $C_{12}H_{14}NO_2$ (Δ0.0 mmu). ESI/MS analysis confirmed the molecular weight as 204 (FIG. 21). The molecular formula matched with the molecular formula of the a-unit in Et 743. Thus, the chemical structure of ETM 204 was proposed to be the aromatic ammonium salt derivative shown in Scheme 3. This simple compound (as well as the other metabolites) can easily be monitored to assay the breakdown of Et 743 in vivo.

Scheme 3

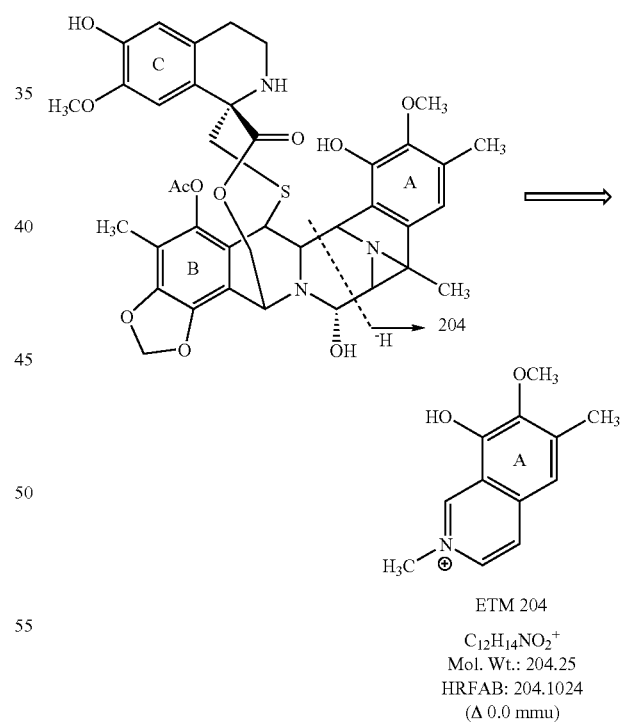

ETM 204
$C_{12}H_{14}NO_2^+$
Mol. Wt.: 204.25
HRFAB: 204.1024
(Δ 0.0 mmu)

Figure 22B:
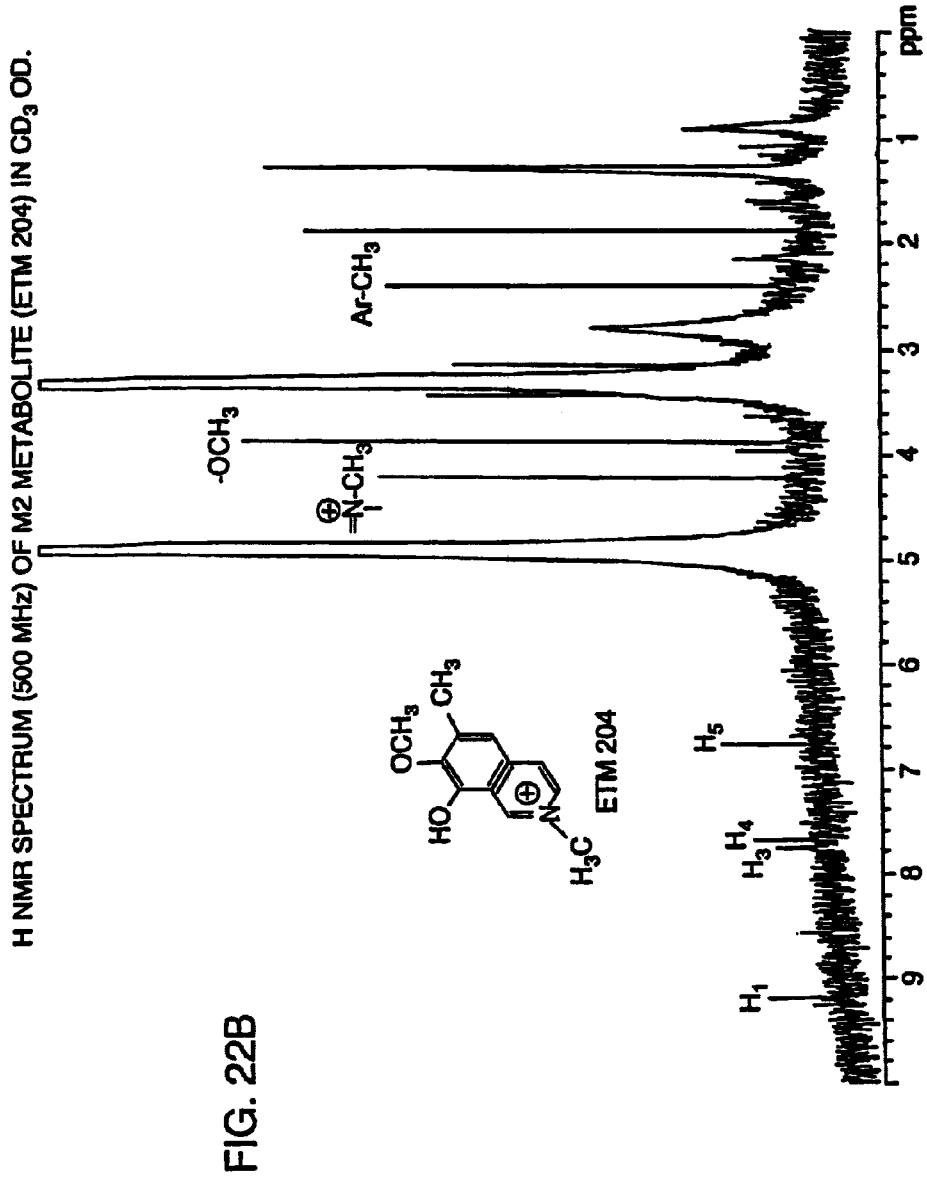
FIG. 22 is the $^1$H NMR spectrum (500 MHz) of ETM 204 in $CD_3OD$.
Figure 23:
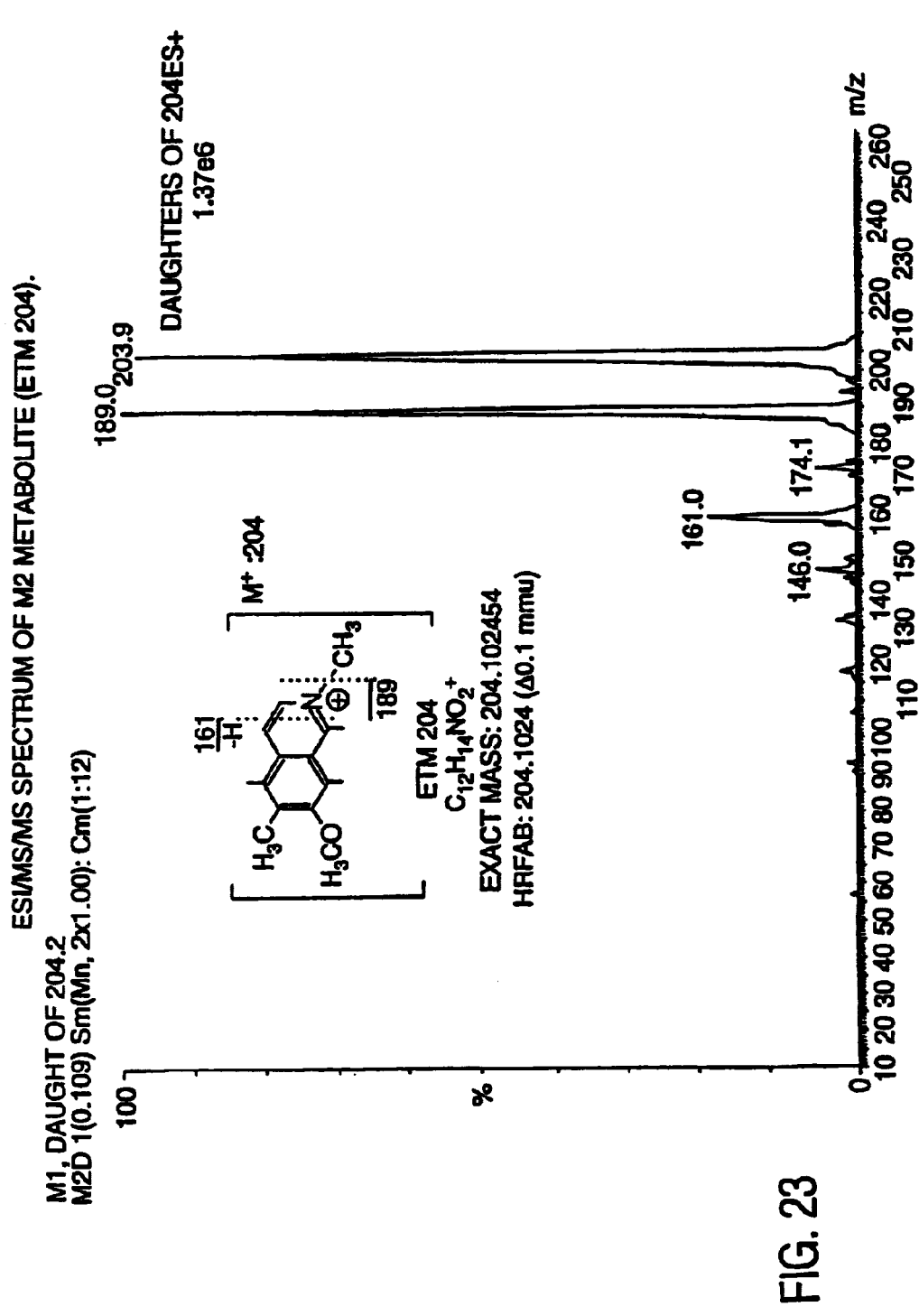
FIG. 23 is the ESI/MS/MS spectrum of ETM 204.

A $^1$H NMR spectrum (FIG. 22) of ETM 204 showed resonances that supported the proposed structure: four aromatics signals (δ 9.2, s; δ 7.8, d, J=5 Hz, and δ 6.8, s) and three methyl singlets (δ 4.2, δ 3.9 and δ 2.4) The ESI/MS/MS of ETM 204 (FIG. 23) showed a prominent peak ion at 189 corresponding to the apparent loss of the N-methyl group (204-$CH_3$).

Biological Studies of ETM-305 and ETM-775:

Compounds ETM-305 and ETM-775 have been assayed employing standard protocols for the following tumor cell lines; P-388 (murine leukemia); A-549 (human lung carcinoma); HT-29 (human colon adenocarcinoma); and MEL-28 (human malignant melanoma). See, for example, Bergeron et al., *Biochem. Biophys. Res. Comm.*, 1984, 121 (3) 848–854 and Schroeder et al., *J. Med. Chem.*, 1981, 24 1078–1083. These results are shown below in Table 2:

TABLE 2

| | Cell Line & Activity $IC_{50}$ (µg/ml) | | | |
|---|---|---|---|---|
| Compound: | P-388 | A-549 | HT-29 | MEL-28 |
| ETM-305 | 0.5 | 0.5 | 0.5 | 0.25 |
| ETM-775 | 0.01 | 0.01 | 0.01 | 0.01 |

Methods of Treatment

The present invention includes bioactive compounds, and accordingly, an embodiment of the present invention is directed to methods of treatment using such compounds. As described above, the compounds of the present invention have exhibited in vitro cytotoxicity against tumor cell lines. It is anticipated that these in vitro activities will likewise extend to in vivo utility.

These compounds have been isolated in substantially pure form, i.e., at a purity level sufficient to allow physical and biological characterization thereof. These compounds have been found to possess specific antitumor activities and as such they will be useful as medicinal agents in mammals, particularly in humans thus, another aspect of the present invention concerns pharmaceutical compositions containing the active compounds identified herein and methods of treatment employment such pharmaceutical compositions.

As described above, the active compounds of the present invention exhibit antitumor activity. thus, the present invention also provides a method of treating any mammal affected by a malignant tumor sensitive to these compounds, which comprises administering to the affected individual a therapeutically effective amount of an active compound or mixture of compounds, or pharmaceutical compositions thereof. The present invention also relates to pharmaceutical preparations, which contain as active ingredient one or more of the compounds of this invention, as well as the processes for its preparation.

Example of pharmaceutical compositions include any solid (tablets, pills, capsules, granules, etc.) or liquid (solutions, suspensions of emulsions) with suitable composition or oral, topical or parenteral administration, and they may contained the pure compound or in combination with any carrier of other pharmacologically active compounds. These compositions may need to be sterile when administered parenterally.

The terms "unit dose" as it pertains to the present invention refers to physically discrete units suitable as unitary dosages for animals, each unit containing a predetermined quantity of active material calculated to produce the desired antitumor effect in association with the required diluent; i.e., carrier, or vehicle. The specifications for the novel unit dose of this invention are dictated by and are directly dependent on (a) the unique characteristics of the active material and the particular antitumor effect to be achieved, and (b) the limitations inherent in the art of compounding such active material for antitumor use in animals.

Unit dosage forms are typically prepared from the frozen or dried active compound (or salts thereof by dispersement in a physiologically tolerable (i.e., acceptable) diluent or vehicle such as water, saline or phosphate-buffered saline to form an aqueous composition. Such diluents are well known in the art and are discussed, for example, in Remington's Pharmaceutical Sciences, 16th Ed., Mack Publishing Company, Easton, Pa. (1980) at pages 1465–1467.

Dosage forms can also include an adjuvant as part of the diluent. Adjuvants such as complete Freund's adjuvant (CFA), incomplete Freund's adjuvant (IFA) and alum are materials well known in the art, and are available commercially from several sources.

The quantity of active compound to be administered depends, inter alia, on the animal species to be treated, the subject animal's size, the size of the tumor (if known), the type of tumor (e.g., solid) present, and the capacity of the subject to utilize the active compound. Precise amounts of active compound required to be administered depend on the judgment of the practitioner and are peculiar to each individual, particularly where humans are the treated animals. Dosage ranges, however, can be characterized by a therapeutically effective blood concentration and can range from a concentration of from about 0.01 µM to about 100 µM, preferably about 0.1 µM to 10 µM.

Suitable regimes for initial administration and booster injections are also variable, but are typified by an initial administration followed by repeated doses at one or more hour intervals by a subsequent injection or other administration. Alternatively, continuous intravenous infusion sufficient to maintain a therapeutically effective concentration in the blood are contemplated.

REFERENCES

The following background references are provided to assist the reader in understanding this invention. To the extent necessary, the contents are hereby incorporated herein by reference.

1. A) Rinehart et al., *J. Org. Chem.* 1990, 55, 4512. B) Rinehart et al., *J. Am. Chem Soc.*, 1996, 118 9017.
2. Herbert et al., *J. Chem. Soc. Perkin Trans. I*, 1987, 1593.
3. Pretsch et al. *Tables of Spectral Data for Structure Determination of Organic Compounds*; Springer-Verla: Berlin, 1989; p. H125.
4. Rinehart et al., *Biochem. Res. Commun.*, 1984, 124, 350.

The present invention has been described in detail, including the preferred embodiments thereof. However, it will be appreciated that those skilled in the art, upon consideration of the present disclosure, may make modifications and/or improvements on this invention and still be within the scope and spirit of this invention.

What is claimed is:

1. Substantially pure ETM-204, having the following structure:

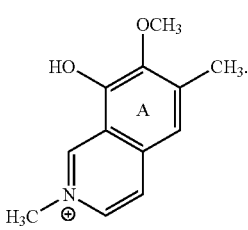

ETM 204

2. A pharmaceutical composition comprising ETM-204 and a pharmaceutically acceptable carrier, diluent, or excipient.

* * * * *